(12) United States Patent
Bozik et al.

(10) Patent No.: US 10,980,783 B2
(45) Date of Patent: *Apr. 20, 2021

(54) COMPOSITIONS AND METHODS FOR TREATING CONDITIONS RELATED TO INCREASED EOSINOPHILS

(71) Applicant: KNOPP BIOSCIENCES LLC, Pittsburgh, PA (US)

(72) Inventors: Michael E. Bozik, Pittsburgh, PA (US); Gregory Hebrank, Greensburg, PA (US); Wildon Farwell, Wayland, MA (US); Thomas Petzinger, Jr., Pittsburgh, PA (US); Steven Dworetzky, Jefferson Hills, PA (US)

(73) Assignee: KNOPP BIOSCIENCES LLC, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/460,473

(22) Filed: Jul. 2, 2019

(65) Prior Publication Data

US 2019/0321339 A1 Oct. 24, 2019

Related U.S. Application Data

(63) Continuation of application No. 15/181,526, filed on Jun. 14, 2016, now Pat. No. 10,383,856, which is a continuation of application No. 13/966,229, filed on Aug. 13, 2013, now Pat. No. 9,468,630.

(60) Provisional application No. 61/845,944, filed on Jul. 12, 2013, provisional application No. 61/859,158, filed on Jul. 26, 2013, provisional application No. 61/865,118, filed on Aug. 12, 2013.

(51) Int. Cl.
*A61K 31/428* (2006.01)
*A61P 29/00* (2006.01)
*A61K 45/06* (2006.01)
*A61P 37/08* (2006.01)

(52) U.S. Cl.
CPC ............ *A61K 31/428* (2013.01); *A61K 45/06* (2013.01)

(58) Field of Classification Search
CPC ......... A61K 31/428; A61P 29/00; A61P 37/08
See application file for complete search history.

(56) References Cited

U.S. PATENT DOCUMENTS

| | | |
|---|---|---|
| 3,598,122 A | 8/1971 | Zaffaroni |
| 3,598,123 A | 8/1971 | Zaffaroni |
| 3,731,683 A | 5/1973 | Zaffaroni |
| 3,797,494 A | 3/1974 | Zaffaroni |
| 4,031,894 A | 6/1977 | Urquhart et al. |
| 4,144,317 A | 3/1979 | Higuchi et al. |
| 4,201,211 A | 5/1980 | Chandrasekaran et al. |
| 4,286,592 A | 9/1981 | Chandrasekaran |
| 4,314,557 A | 2/1982 | Chandrasekaran |
| 4,327,725 A | 5/1982 | Cortese et al. |
| 4,379,454 A | 4/1983 | Campbell et al. |
| 4,395,859 A | 8/1983 | Rohrer |
| 4,435,180 A | 3/1984 | Leeper |
| 4,559,222 A | 12/1985 | Enscore et al. |
| 4,568,343 A | 2/1986 | Leeper et al. |
| 4,573,995 A | 3/1986 | Chen et al. |
| 4,588,580 A | 5/1986 | Gale et al. |
| 4,612,008 A | 9/1986 | Wong et al. |
| 4,626,539 A | 12/1986 | Aungst et al. |
| 4,645,502 A | 2/1987 | Gale et al. |
| 4,698,062 A | 10/1987 | Gale et al. |
| 4,704,282 A | 11/1987 | Campbell et al. |
| 4,725,272 A | 2/1988 | Gale |
| 4,731,374 A | 3/1988 | Griss et al. |
| 4,781,924 A | 11/1988 | Lee et al. |
| 4,783,337 A | 11/1988 | Wong et al. |
| 4,788,062 A | 11/1988 | Gale et al. |
| 4,806,341 A | 2/1989 | Chien et al. |
| 4,816,258 A | 3/1989 | Nedberge et al. |
| 4,843,086 A | 6/1989 | Griss et al. |
| 4,849,226 A | 7/1989 | Gale |
| 4,886,812 A | 12/1989 | Griss et al. |
| 4,904,475 A | 2/1990 | Gale et al. |
| 4,908,027 A | 3/1990 | Enscore et al. |
| 4,917,895 A | 4/1990 | Lee et al. |
| 4,938,759 A | 7/1990 | Enscore et al. |
| 4,943,435 A | 7/1990 | Baker et al. |
| 5,004,610 A | 4/1991 | Osborne et al. |
| 5,024,843 A | 6/1991 | Kuczynski et al. |
| 5,069,909 A | 12/1991 | Sharma et al. |
| 5,071,656 A | 12/1991 | Lee et al. |
| 5,082,668 A | 1/1992 | Wong et al. |

(Continued)

FOREIGN PATENT DOCUMENTS

| | | |
|---|---|---|
| AU | 2002360600 B2 | 11/2007 |
| AU | 2006279643 B2 | 6/2010 |

(Continued)

OTHER PUBLICATIONS

Schneider et al. "Dopamine Autoreceptor Agonists: Resolution and Pharmacological Activity of 2,6-Diaminotetrahydrobenzothiazole and an Aminothiazole Analogue of Apomorphine" 1987, J. Med. Chem. 30:494-498.

(Continued)

*Primary Examiner* — Jeffrey S Lundgren
*Assistant Examiner* — Chris E Simmons
(74) *Attorney, Agent, or Firm* — Troutman Pepper Hamilton Sanders LLP

(57) ABSTRACT

Disclosed herein are methods of treating diseases associated with increased numbers of eosinophils basophils, and/or neutrophils with R(+) pramipexole.

26 Claims, 19 Drawing Sheets

(56) References Cited

U.S. PATENT DOCUMENTS

| | | |
|---|---|---|
| 5,091,190 A | 2/1992 | Kuczynski et al. |
| 5,112,842 A | 5/1992 | Zierenberg et al. |
| 5,122,382 A | 6/1992 | Gale et al. |
| 5,141,750 A | 8/1992 | Lee et al. |
| 5,284,660 A | 2/1994 | Lee et al. |
| 5,314,694 A | 5/1994 | Gale et al. |
| 5,342,623 A | 8/1994 | Enscore et al. |
| 5,411,740 A | 5/1995 | Lee et al. |
| 5,442,117 A | 8/1995 | Stahly et al. |
| 5,545,413 A | 8/1996 | Kuczynski et al. |
| 5,591,454 A | 1/1997 | Kuczynski et al. |
| 5,635,203 A | 6/1997 | Gale et al. |
| 5,650,420 A | 7/1997 | Hall et al. |
| 5,674,895 A | 10/1997 | Guittard et al. |
| 5,719,060 A | 2/1998 | Hutchens et al. |
| 5,792,664 A | 8/1998 | Chait et al. |
| 5,804,215 A | 9/1998 | Cubbage et al. |
| 5,830,497 A | 11/1998 | Yamanaka et al. |
| 5,840,754 A | 11/1998 | Guittard et al. |
| 5,912,268 A | 6/1999 | Guittard et al. |
| 6,043,251 A | 3/2000 | Douillet et al. |
| 6,156,777 A | 12/2000 | Hall et al. |
| 6,187,802 B1 | 2/2001 | Cheetham et al. |
| 6,197,339 B1 | 3/2001 | Ju |
| 6,228,398 B1 | 5/2001 | Devane et al. |
| 6,255,329 B1 | 7/2001 | Maj |
| 6,262,115 B1 | 7/2001 | Guittard et al. |
| 6,284,774 B1 | 9/2001 | Wright et al. |
| 6,294,790 B1 | 9/2001 | Weinberger |
| 6,443,976 B1 | 9/2002 | Flower et al. |
| 6,458,820 B1 | 10/2002 | Hall et al. |
| 6,480,820 B1 | 11/2002 | Clopton et al. |
| 6,541,486 B1 | 4/2003 | Bitler et al. |
| 6,618,138 B2 | 9/2003 | Khoury |
| 6,667,329 B1 | 12/2003 | Maj |
| 6,675,104 B2 | 1/2004 | Paulse et al. |
| 6,727,367 B2 | 4/2004 | Pospisilik |
| 6,730,325 B2 | 5/2004 | Devane et al. |
| 6,750,235 B1 | 6/2004 | Rosenbaum |
| 6,776,984 B1 | 8/2004 | Schwartz |
| 6,793,936 B2 | 9/2004 | Devane et al. |
| 6,902,742 B2 | 6/2005 | Devane et al. |
| 6,919,092 B2 | 7/2005 | Guittard et al. |
| 6,919,373 B1 | 7/2005 | Lam et al. |
| 6,927,036 B2 | 8/2005 | Gallop et al. |
| 6,929,801 B2 | 8/2005 | Klose et al. |
| 6,930,129 B2 | 8/2005 | Lam et al. |
| 7,005,255 B2 | 2/2006 | Kaddurah-Daouk et al. |
| 7,157,480 B2 | 1/2007 | Bennett, Jr. |
| 7,344,733 B2 | 3/2008 | Beier et al. |
| 7,572,596 B2 | 8/2009 | Bowser |
| 7,741,490 B2 | 6/2010 | Castaldi et al. |
| 8,017,598 B2 | 9/2011 | Bozik et al. |
| 8,186,890 B2 | 5/2012 | Lu |
| 8,192,091 B2 | 6/2012 | Hsu et al. |
| 8,408,815 B2 | 4/2013 | Lin et al. |
| 9,468,630 B2 | 10/2016 | Bozik et al. |
| 2002/0004058 A1 | 1/2002 | Yoshii et al. |
| 2002/0103240 A1 | 8/2002 | Pospisilik |
| 2002/0106731 A1 | 8/2002 | Ruben et al. |
| 2002/0151526 A1 | 10/2002 | Gallop et al. |
| 2002/0177626 A1 | 11/2002 | Cook et al. |
| 2003/0013120 A1 | 1/2003 | Patz et al. |
| 2003/0049318 A1 | 3/2003 | Davis et al. |
| 2003/0166696 A1 | 9/2003 | Warsinsky et al. |
| 2003/0203055 A1 | 10/2003 | Rao et al. |
| 2004/0014721 A1 | 1/2004 | Hensley et al. |
| 2004/0031667 A1 | 2/2004 | Dinkel et al. |
| 2004/0033530 A1 | 2/2004 | Awrey et al. |
| 2004/0067991 A1 | 4/2004 | Greig et al. |
| 2004/0097540 A1 | 5/2004 | Peters et al. |
| 2004/0122104 A1 | 6/2004 | Hirsh et al. |
| 2004/0132788 A1 | 7/2004 | Chabrier De Lassauniere et al. |
| 2004/0132826 A1 | 7/2004 | Hirsh et al. |
| 2004/0219213 A1 | 11/2004 | Burnside et al. |
| 2004/0247656 A1 | 12/2004 | Beier et al. |
| 2004/0265370 A1 | 12/2004 | Odidi et al. |
| 2005/0031667 A1 | 2/2005 | Patel et al. |
| 2005/0032856 A1 | 2/2005 | Bennett |
| 2005/0053649 A1 | 3/2005 | Chalmers |
| 2005/0059717 A1 | 3/2005 | van Eupen et al. |
| 2005/0070715 A1 | 3/2005 | Bhat et al. |
| 2005/0074865 A1 | 4/2005 | Afeyan et al. |
| 2005/0089575 A1 | 4/2005 | Friedl et al. |
| 2005/0148026 A1 | 7/2005 | Bowser et al. |
| 2005/0208156 A1 | 9/2005 | Ploch et al. |
| 2005/0220877 A1 | 10/2005 | Patel et al. |
| 2005/0226926 A1 | 10/2005 | Amidon et al. |
| 2005/0265379 A1 | 12/2005 | Rao |
| 2006/0009659 A1 | 1/2006 | Maywald et al. |
| 2006/0046967 A1 | 3/2006 | Satyam |
| 2006/0051419 A1 | 3/2006 | Friedl et al. |
| 2006/0069263 A1 | 3/2006 | Gribun et al. |
| 2006/0099257 A1 | 5/2006 | Langridge et al. |
| 2006/0106224 A1 | 5/2006 | Gupta et al. |
| 2006/0110450 A1 | 5/2006 | Eisenreich |
| 2006/0121619 A1 | 6/2006 | Bowser |
| 2006/0128643 A1 | 6/2006 | Kaddurah-Daouk et al. |
| 2006/0141037 A1 | 6/2006 | Mehta et al. |
| 2006/0148866 A1 | 7/2006 | Xia et al. |
| 2006/0281797 A1 | 12/2006 | Bennett |
| 2006/0286167 A1 | 12/2006 | Staunton et al. |
| 2007/0087410 A1 | 4/2007 | Lanahan et al. |
| 2007/0105918 A1 | 5/2007 | Bennett, Jr. |
| 2007/0203209 A1 | 8/2007 | Bartolini et al. |
| 2007/0259930 A1 | 11/2007 | Bozik et al. |
| 2008/0014259 A1 | 1/2008 | Bozik et al. |
| 2008/0020028 A1 | 1/2008 | Shevchuk et al. |
| 2008/0026043 A1 | 1/2008 | Mueller et al. |
| 2008/0081041 A1 | 4/2008 | Nemeth |
| 2008/0096939 A1 | 4/2008 | Keil et al. |
| 2008/0194832 A1 | 8/2008 | Silva Guisasola et al. |
| 2008/0227985 A1 | 9/2008 | Raje et al. |
| 2008/0234338 A1 | 9/2008 | Bennett, Jr. |
| 2009/0042956 A1 | 2/2009 | Bozik et al. |
| 2009/0054504 A1 | 2/2009 | Bozik et al. |
| 2009/0105483 A1 | 4/2009 | Balicki et al. |
| 2009/0149518 A1 | 6/2009 | Nishii et al. |
| 2010/0291073 A1 | 11/2010 | Koike et al. |
| 2010/0292149 A1 | 11/2010 | Bowser |
| 2011/0009460 A1 | 1/2011 | Gribkoff et al. |
| 2011/0020339 A1 | 1/2011 | Hargreave et al. |
| 2011/0190356 A1 | 8/2011 | Bozik et al. |
| 2011/0218222 A1 | 9/2011 | Bennett, Jr. |
| 2011/0224268 A1 | 9/2011 | Bozik et al. |
| 2011/0293718 A1 | 12/2011 | Bozik et al. |
| 2011/0301210 A1 | 12/2011 | Bennett, Jr. |
| 2012/0134929 A1 | 5/2012 | McGrath et al. |
| 2012/0142715 A1 | 6/2012 | Kim |
| 2012/0148575 A1 | 6/2012 | Koike et al. |
| 2012/0225915 A1 | 9/2012 | Bozik et al. |
| 2012/0253047 A1 | 10/2012 | Allegrini et al. |
| 2012/0258994 A1 | 10/2012 | McKinney et al. |
| 2013/0059801 A1 | 3/2013 | Milne et al. |
| 2013/0079526 A1 | 3/2013 | Greenfield et al. |
| 2013/0116292 A1 | 5/2013 | Bennett, Jr. |
| 2013/0123312 A1 | 5/2013 | Bozik et al. |
| 2013/0172394 A1 | 7/2013 | Bennett, Jr. |
| 2013/0230569 A1 | 9/2013 | Bozik et al. |
| 2013/0245081 A1 | 9/2013 | Gribkoff et al. |
| 2013/0273557 A1 | 10/2013 | Gribkoff et al. |
| 2013/0310430 A1 | 11/2013 | Bozik et al. |
| 2014/0018343 A1 | 1/2014 | Romero et al. |
| 2014/0031401 A1 | 1/2014 | Bozik et al. |
| 2014/0100372 A1 | 4/2014 | Raje et al. |
| 2014/0329869 A1 | 11/2014 | Bozik et al. |
| 2015/0018397 A1 | 1/2015 | Bozik et al. |
| 2015/0126745 A1 | 5/2015 | Chen et al. |
| 2016/0022647 A1 | 1/2016 | Bozik et al. |
| 2016/0030397 A1 | 2/2016 | Bozik et al. |
| 2016/0158205 A1 | 6/2016 | Bozik et al. |

(56) References Cited

U.S. PATENT DOCUMENTS

| | | | |
|---|---|---|---|
| 2016/0193186 A1 | 7/2016 | Bozik et al. | |
| 2016/0193187 A1 | 7/2016 | Bozik et al. | |

FOREIGN PATENT DOCUMENTS

| | | | |
|---|---|---|---|
| AU | 2007333050 B2 | 8/2013 | |
| CA | 2605078 A1 | 10/2006 | |
| CA | 2619217 A1 | 2/2007 | |
| CN | 1308533 A | 8/2001 | |
| CN | 1617720 A | 5/2005 | |
| CN | 1735604 A | 2/2006 | |
| CN | 101641096 A | 2/2010 | |
| CN | 101677564 A | 3/2010 | |
| CN | 102160865 A | 8/2011 | |
| CN | 102772404 A | 11/2012 | |
| EP | 0186087 B1 | 8/1989 | |
| EP | 0558861 A1 | 9/1993 | |
| EP | 1453505 A4 | 1/2007 | |
| EP | 2156833 A1 | 2/2010 | |
| EP | 2305252 A1 | 4/2011 | |
| EP | 2465500 A1 | 6/2012 | |
| EP | 2497472 A1 | 9/2012 | |
| EP | 2497473 A1 | 9/2012 | |
| EP | 2497474 A1 | 9/2012 | |
| EP | 2542541 A1 | 1/2013 | |
| EP | 2442655 A4 | 4/2013 | |
| EP | 2246053 B1 | 9/2013 | |
| JP | H07504655 A | 5/1995 | |
| JP | H10510809 A | 10/1998 | |
| JP | 2006143708 A | 6/2006 | |
| JP | 2009504748 A | 2/2009 | |
| JP | 2010031059 A | 2/2010 | |
| JP | 2010513316 A | 4/2010 | |
| JP | 4500543 B2 | 7/2010 | |
| JP | H11515012 | 5/2011 | |
| JP | 6115377 B2 | 6/2017 | |
| RU | 2009126742 A | 1/2011 | |
| WO | 1993017683 A1 | 9/1993 | |
| WO | 1993024834 A1 | 12/1993 | |
| WO | 1996018395 A1 | 6/1996 | |
| WO | 1997015304 A1 | 5/1997 | |
| WO | 1998059360 A1 | 4/1999 | |
| WO | 2001013902 A2 | 3/2001 | |
| WO | 2001022820 A1 | 4/2001 | |
| WO | 2001062249 A1 | 8/2001 | |
| WO | 2003049705 A2 | 6/2003 | |
| WO | 2004002520 A1 | 1/2004 | |
| WO | 2003070188 A2 | 2/2004 | |
| WO | 2004010999 A1 | 2/2004 | |
| WO | 2004041797 A1 | 5/2004 | |
| WO | 2004026246 A2 | 7/2004 | |
| WO | 2004058163 A2 | 10/2004 | |
| WO | 2005011687 A1 | 2/2005 | |
| WO | 2004050034 A2 | 4/2005 | |
| WO | 2005092871 A2 | 12/2005 | |
| WO | 2005123193 A2 | 3/2006 | |
| WO | 2006043532 A1 | 4/2006 | |
| WO | 2006012277 A2 | 8/2006 | |
| WO | 2006003471 A2 | 9/2006 | |
| WO | 2006015943 A2 | 2/2007 | |
| WO | 2006015944 A2 | 2/2007 | |
| WO | 2007022182 A1 | 2/2007 | |
| WO | 2007045620 A1 | 4/2007 | |
| WO | 2006076681 A2 | 6/2007 | |
| WO | 2007075095 A1 | 7/2007 | |
| WO | 2007076062 A2 | 7/2007 | |
| WO | 2006116369 A2 | 8/2007 | |
| WO | 2007137071 A2 | 11/2007 | |
| WO | 2007090882 A2 | 12/2007 | |
| WO | 2008023027 A2 | 2/2008 | |
| WO | 2008041240 A1 | 4/2008 | |
| WO | 2008052953 A1 | 5/2008 | |
| WO | 2008074033 A1 | 6/2008 | |
| WO | 2008113003 A1 | 9/2008 | |
| WO | 2008113056 A2 | 9/2008 | |
| WO | 2007121188 A2 | 11/2008 | |
| WO | 2008104847 A2 | 2/2009 | |
| WO | 2010022140 A1 | 2/2010 | |
| WO | 2010148409 A1 | 12/2010 | |
| WO | 2011109596 A1 | 9/2011 | |
| WO | 2011150221 A2 | 2/2012 | |
| WO | 2012019015 A3 | 5/2012 | |
| WO | 2013034550 A1 | 3/2013 | |
| WO | 2013096816 A1 | 6/2013 | |
| WO | 2013096870 A1 | 6/2013 | |
| WO | 2014134569 A1 | 9/2014 | |
| WO | 2015006708 A1 | 1/2015 | |
| WO | 2015023786 A1 | 2/2015 | |
| WO | 2015023790 A1 | 2/2015 | |
| WO | 2015061777 A1 | 4/2015 | |

OTHER PUBLICATIONS

Schuelke et al. "Myostatin Mutation Associated With Gross Muscle Hypertrophy in a Child" 2004, N. Engl. J. Med. 350:2682-2688 (Para.1).

Shannon et al. "Efficacy of Pramipexole, a Novel Dopamine Agonist, as Monotherapy in Mild to Moderate Parkinson's Disease" 1997, Neurology 49(3)a;724-728.

Sousa et al. "Deposition of transthyretin in early stages of familial amyloidotic polyneuropathy: evidence for toxicity of nonfibrillar aggregates" Dec. 2001, Am J Pathol. 159(6):1993-2000.

Sousa et al. "Evidence for early cytotoxic aggregates in transgenic mice for human transthyretin Leu55Pro" Nov. 2002, Am. J. of Pathol. 161(5):1935-1948.

Stein et al. "Neutralization of transthyretin reverses the neuroprotective effects of secreted amyloid precursor protein (APP) in APPsw mice resulting in tau phosphorylation and loss of hippocampal neurons: Support for the amyloid hypothesis" Sep. 1, 2004, J. Neurosci. 24(35):7707-7717.

The Foundation Fighting Blindness "Animal Models for Studying Inherited Degenerative Retinal Disease" 2000 (printed from www.retina-international.org/sci-news/animmod.doc on Jan. 11, 2009) The Foundation Fighting Blindness (23 pages).

Tobran-Tink et al. "Neuroprotection in Macular Degeneration" 2005, Age-Related Macular Degeneration: A Comprehensive Textbook (Lippincott Williams & Wilkins), 29:335-336.

Tsuzuki et al. "Structure of the Human Prealbumin Gene" Oct. 5, 1984, J. Biol. Chem. 260(22):12224-12227.

U.S. Dept. of HHS FDA CDER (Guidance for Industry), Jul. 2005, 30 pp.

Uemichi et al. "A New Mutant Transthyretin (Arg 10) Associated with Familial Amyloid Polyneuropathy" 1992, J. Med. Genet. 29:888-891.

Voskoglou-Nomikos et al., "Clinical Predictive Value of the in Vitro Cell Line, Human Xenograft, and Mouse Allograft Preclinical Cancer Models", Clinical Cancer Research (Sep. 15, 2003), 9:4227-4239.

Wang et al. "R+ pramipexole as a mitochondrially focused neuroprotectant: initial early phase studies in ALS" Feb. 2008, Amyotroph Lateral Scler. 9(1):50-58.

Wedi et al. "Chronic urticarial serum induces histamine release, leukotriene production, and basophil CD63 surface expression-inhibitory effects of anti-inflammatory drugs" Journal of allegery and clinical immunology, Mar. 2000, 105(3):552-560.

Winkler et al. "Oxidative damage and age-related macular degeneration" Nov. 3, 1999, Mol. Vis. 5:32 (Abstract only).

Wong "A 384-well cell-based phosphor-ERK assay for dopamine D2 and D3 receptors" 2004, Analytical Biochem. 333:265-272.

Wong et al. "Activation of Extracellular Signal-Regulated Kinase by Dopamine D2 and D3 Receptors" 2003, Society for Neuroscience Abstracts (retrieved on line at sfn.scholarone.com/itin2003/main.html?new.sub.—page.sub.—d=126&abstrac-t.sub.—id=3866&p.sub.—num=363.4&is.sub.—tech= on Jun. 23, 2008).

Worker "Novel Therapeutic Strategies" 1999, IDRUGS, Current Drugs Ltd. GB 2(9):848-852.

(56) References Cited

OTHER PUBLICATIONS

Wright et al. "Influence of Probenecid (PR) and Cimetidine (C) on Pramipexole (PX) Pharmacokinetics" Feb. 1995, Clin. Pharmacol. & Ther. 59(2):PII-99 (abstract only).
Zheng et al. "Purification and identification of an estrogen binding protein from rat brain: oligomycin sensitivity-conferring protein (OSCP), a subunit of mitochondrial F0F1-ATP synthase/ATPase" Jan. 1999, J. Ster. Biochem. Mol. Biol.68(1-2):65-75.
Abrahamson et al. "Structure and expression of the human cystatin C gene" 1990, Biochem J. 268(2):287-294.
Abramova et al. "Inhibition by R(+) or S(−) Pramipexole of Caspase Activation and Cell Death Induced by Methylpyridinium Ion or Beta Amyloid Peptide in SH—SY5Y Neuroblastoma" 2002, J. Neuroscience Res. 67(4):494-500.
Agardh et al. "Expression of antioxidant enzymes in rat retinal ischemia followed by reperfusion" Jul. 2006, Metabolism 55(7):892-898 (Abstract).
Aguila et al. "Prognosis in Amyotrophic Lateral Sclerosis: A population based study" 2003, Neurology 60:813-819.
Akintola-Ogunremi et al. "Chronic lymphocytic leukemia presenting with symptomatic centeral nervous system involvement" 2002, Ann. Hematol. 81:402-404.
Anonymous "Variant of Parkinson's Drug Tested in ALS" Jul. 19, 2006 (printed from v1/v1/w.als mda.org/researc! 1 /news/0607 • 19als Qramii;;:exole.html on Feb. Oct. 8, 2121) (Abstract).
Anosova et al. "Antigenecity and Immunogenicity of Allogeneic Retinal Transplants" Oct. 2001, J. Clin. Invest. 108(8):1175-1183.
Ansel et al. "Pharmaceutical Dosage Forms and Drug Delivery Systems, 61; n; ed." 1995, Williams and Wilkins Media, Malvern, PA (TOC).
Anthony et al. "Protective Immune Mechanisms in Helminth Infection" Dec. 2007, Nat Rev Immunol. 7(12):975-987.
Arico et al. Restless Legs Syndrome as the Presenting Symptom of Multiple Myeloma 2013, Journal of Clinical Sleep Medicine 9(4):383-385.
Arimal et al. "Eosinophilic and ubiquitinated neuronal inclusions in motor and extra-motor cortices in a brain with amyotrophic lateral sclerosis" Brain Pathology (1997) 1074.
Asgeirsson et al. "Hereditary cystatin C amyloid angiopathy: monitoring the presence of the Leu-68-7Gln cystatin C variant in cerebrospinal fluids and monocyte cultures by MS" 1998, Biochem. J, 329 (Pt 3):497-503 (1998).
Ashcroft et al. "An Efficient and Scalable Synthesis of the Endothelin Antagonists UK-350,926 and UK-349,862 Using a Dynamic Resolution Process" 2005, Organic Proc. Res. & Dev. 9:663-669.
Balicki et al. "A New, Efficient and Economic Method for Preparation of Pramipexole" May 16, 2006, Book of Abstracts: The Fifth Multidisciplinary conference on Drug Research, Pielaszek Research (Warszawa, Poland) Poster No. 1-19, p. 30 (English Abstract).
Balicki et al. "New method for preparing pramipexole dihydrochloride monohydrate" 2006, Przemysl Chemiczny 85(5):344-346.
Banker et al. "Modern Pharmaceutics" 1979, Marcel Dekker, Inc. (TOC).
Beal "Oxidative Metabolism" 2000, Ann. N.Y. Acad. Sci. 924:164-169.
Beatty et al. "The Role of Oxidative Stress in the Pathogenesis of Age-Related Macular Degeneration" 2000, Surv. Opthalmol 45(2):115-134.
Benson et al. "Identification of carriers of a variant plasma prealbumin (transthyretin) associated with familial amyloidotic polyneuropathy type J" 1985,; J. Clin. Invest. 74:71-75.
Berge et al., Pharmaceutical Salts, 1977, J. Pharm. Sciences 66(1):1-19.
Bergen et al. "Identification of transthyretin variants by sequential proteomic and genomic analysis" 2004, Clin. Chem. 50(9):1544-1552.
Bernstein et al. "Transythyretin: Its response to malnutrition and stress injury. Clinical usefulness and economic Implications" Dec. 2002, Clin. Chem. Lab. Med. 40(12):1344-1348.

Biglan et al. "A Review of Pramipexole and its Clinical Utility in Parkinson's Disease" 2002, Expert Opinion Pharmacotherapy 3(2):197-210.
Borchelt et al. "Superoxide dismutase 1 with mutations linked to familial amyotrophic lateral sclerosis possesses significant activity" 1994, PNAS USA 91(17):8292-8296.
Bozik et al. "Safety, Tolerability, and Pharmacokinetics of KNS-760704 (Dexpramipexole) in Healthy Adult Subjects" 2011, J. Clin. Pharmacol. 51:1177-1185.
Brooks "El Escorial rld Federation of Neurology Criteria for the Diagnosis of Amyotrophic Lateral Sclerosis" 1994, Journal of the Neurlogical Sciences 124(Suppl.):96-107.
Brooks et al. "El Escorial revisited: Revised criteria for the diagnosis of amotrophic lateral sclerosis" 2000, ALS and other motor neuron disorders 1:293-299.
Carvey, et al. "Attenuation of levodopa-induced toxicity in mesencephalic cultures by pramipexole" 1997, J. Neural. Transm. 209-228.
Cassarino et al. "An evaluation of the role of mitochondria in neurodegenerative diseases: mitochondrial mutations and oxidative pathology, protective nuclear responses, and cell death in neurodegeneration" 1999, Brain Res. Rev. 29:1-25.
Cassarino et al. "Cyclosporin A increases resting mitochondrial membrane potential in SY5Y cells and reverses the depressed mitochondrial membrane potential of Alzheimer's disease cybrids" May 13, 1998, Biochem. and Biophysical Research Comm.248:168-173.
Cassarino et al. "Interaction among mitochondria, mitogen-activated protein kinases, and nuclear factor-kappaB in cellular models of Parkinson's disease" Apr. 2000, J Neurochem 74(4):1384-92.
Cassarino et al. "Pramipexole reduces reactive oxygen species production in vivo and in vitro and inhibits the mitochondrial permeability transition produced by the parkinsonian neurotoxin methylpyridinium ion" 1998, J. Neurochem. 71(1):295-301.
Cleveland et al. "From Charcot to Lou Gehrig: deciphering selective motor neuron death in ALS" Nov. 2001, Nature 2:806-819.
Corcoran et al. "Absence of retinoids can induce motoneuron disease in the adult rat and a retinoid defect is present in motoneuron disease patients" 2002, J. Cell. Sci. 115:4735-4741.
Corrigan et al. "Comparison of Pramipexole, Fluoxetine, and Placebo in Patients with Major Depression" 2000, Depression and Anxiety 11:58-65.
Cudkowicz et al. "Dexpramipexole versus placebo for patients with amyotrophic lateral sclerosis (EMPOWER): a ramdomised double-blind phase 3 trial" 2013, Lancet Neurol. 12:1059-1067.
Cudkowicz et al. "Measures and Markers in Amyotrophic Lateral Sclerosis" 2004, NeuroRx: The Journal of the American Society for Experimental Neuro Therapeutics 1(2):273-283.
Cudkowicz et al. "The effects of dexpramipexole (KNS-760704) in individuals with amyotrophic lateral sclerosis" 2011 Nature Medicine 17:1652-1656.
Danzeisen et al. "Targeted Antioxidative and Neuroprotective Properties of the Dopamine Agonist Pramipexole and its Nondopaminergic Enantiomer SND919CL2x [(+)2-Amino-4, 5, 6, 7-tetrahydro-6-L-propylamino-benzathiazole Dihydrochloride]" 2006, J. Pharmacol. Exp. Ther. 316:189-199.
Davis et al. "Eosinophils and Cancer" Aug. 20, 2014, Cancer Immunol Res. 2(1):1-8.
Declaration of James P. Bennett Under 37 C.F.R. 1.132 dated Dec. 15, 2009.
Deigner et al. "Apoptosis Modulators in the Therapy of Neurodegenerative Diseases" Apr. 2000, Ex. Opin. investigational Drugs 9(4):747-764.
Deng et al. "Elevation of cystatin C in susceptible neurons in Alzheimer's disease" Sep. 2001, Am. J. Pathol. 159(3):1061-1068.
Dooley et al. "Pramipexole. A Review of its Use in the Managemetn of Early and Advanced Parkinson's Disease" Jun. 1998, Drugs Aging 12(6):495-514. (abstract only).
Drobny et al. "Possible Extrapyramidal System Degradation in Parkinson's Disease" 2000, Brain Research Bulletin 53(4):425-430.
Email correspondence from James P. Bennett to Michael Bozik dated Apr. 6, 2007 with a draft manuscript entitled "R(+) Pramipexole

(56) References Cited

OTHER PUBLICATIONS as a Neuroprotectant I: Effects of R(+) Pramipexole Treatment of ALS on ALSFRSr Forced Vital Capacity and Neurophysiological Index".

Email correspondence from James P. Bennett to Michael Bozik dated Apr. 6, 2007 with a draft manuscript entitled "R(+) Pramipexole as a Neuroprotectant II: Tolerability and Pharmacokinetics in ALS of Esclating Doses to 300mgday".

Email correspondence from James P. Bennett to Michael Bozik dated May 11, 2006 with a presentation entitled "ALS: An Investigator's View of the Disease and its Treatment".

Email correspondence from James P. Bennett to Michael Bozik dated Oct. 9, 2006 with a draft grant application.

European Seach Report and Opinion dated Aug. 1, 2012 for EP 12163888.

Levy et al. "Stroke in Icelandic Patients With Hereditary Amyloid Angiopathy is Related to a Mutation in the Cystatin C Gene, An Inhibitor of Cysteine Proteases" 1989, The Journal of Experimental Medicine 169(5):1771-1778.

Liang et al. "Oxidative stress-induced mitochondrial DNA damage in human retinal pigment epithelial cells: a possible mechanism for RPE aging and age-related macular degeneration" 2003, Exp. Eye Res. 76(4):397-403.

Lieberman et al. "Clinical evaluation of pramipexole in advanced Parkinson's disease: Results of a double-blind, placebo-controlled, parallel-group study" 1997, Neurology 49:162-168.

Lieberman et al. "Pharmaceutical Dosage Forms: Disperse Systems" 1996, Marcel Dekker, Inc., New York vol. 2 (TOC).

Lieberman et al. "Pharmaceutical Dosage Forms: Tablets" 1989 Marcel Dekker Inc. New York vol. 1 (TOC).

Lin et al. "Large-scale protein identification using mass spectrometry" 2003, Biochimica et Biophysica Acta 16460-2):1-10.

Liou et al. "Case Report Churg-Strauss syndrome presented as multiple intracerebral hemorrhage" (1997) Lupis 6:279-282.

Liu et al. "Eosinophil-Derived Neurotoxin is Elevated in Patients with Amyotrophic Lateral Sclerosis" Feb. 21, 2013, Mediators of Inflammation 2013:1-7.

Lofberg, et al. "Immunohistochemical characterization of the amyloid deposits and quantitation of pertinent cerebrospinal fluid proteins in hereditary cerebral hemorrhage with amyloidosis" 1987, Stroke 18(2):431-440.

Lomen-Hoerth "Amyotrophic lateral sclerosis from bench to bedside" 2008, Semin. Neurol. 28(2):205-211.

Love "Oxidative Stress in Brain Ischemia" Apr. 5, 1999, Brain Pathology 9(1)119-131 (Abstract only).

Lucchinetti et al. "Inflammatory Cortical Demyelination in Early Multiple Sclerosis" 2011, The New England Journal of Medicine 365:2188-2197.

Malaspina et al. "Differential expression of 14 genes in amyotrophic lateral sclerosis spinal cord detected using gridded eDNA arrays" 2001, J. Neurochemistry 77(1):132-145.

Martens "Cloning and Sequence Analysis of Human Pituitary eDNA Encoding the Novel Polypeptide 7B2" 1988, FEBS Letters 234(1):160-164.

Martens et al. "The novel pituitary polypeptide 7B2 is a highly-conserved protein coexpressed with proopiomelanocortin" Apr. 1989, Eur. J. Biochem. 181(1):75-79.

Masi et al. "The American College of Rheumatology 1990 Criteria for the Classification of Churg-Strauss Syndrome (Allergic Granulomatosis and Angiitis)" Aug. 1990, Arthritis Rheum. 33(8):1094-1100.

Matthews et al. "Assessment of the Health Effects of Chemicals in Humans: I. Qsar Estimation of the Maximum Recommended Therapeutic Dose (MRTD) and No Effect Level (NOEL) of Organic Chemicals Based on Clinical Trial Data" 2004, Current DrugDiscovery Technologies 1:61-76.

Mbikay et al. "Neuroendocrine secretory protein 7B2: structure, expression and functions" Jul. 15, 2001, Biochem J. 357(2):329-342.

Menzies et al. "Mitochondrial dysfunction in a cell culture model of familial amyotrophic lateral sclerosis" Jul. 2002, Brain 125(7):1522-1533.

Merck Manuals Online Medical Library, Age-Related Macular Degeneration (ARMD), 2005, printed Aug. 13, 2008 from http://www.merck.com/mmpe/print/sec09/ch106/ch106b.html, 2 pages.

Mey et al. "Retinoic Acid Signaling in the Nervous System of Adult Vertebrates" 2004, The Neuroscientist 10(5):409-421.

Mhatre et al. "Oxidative Stress and Neuroinflammation in Alzheimer's Disease and Amyotrophic Lateral Sclerosis; Common Links and Potential Therapeutic Targets" Apr. 2004, J. Alzheimers Dis. 6(2):147-157 (abstract only).

Mierau at al., Pramipexole binding and activation of cloned and expressed dopamine $D_2$, $D_3$ and $D_4$ receptors, 1995, Eur. J. Pharmacol. 290:29-36.

Miklya et al. "A pharmacological analysis elucidating why, in contrast to (−)-deprenyl (selegiline), .alpha.-tocopherol was ineffective in the DATATOP study" 2003, Life Sciences 72:2641-2648.

MIRAPEX® Prescribing Information from Boehringer Ingelheim 2006 http:www.biopsychiatry.compramipexole-mirapex.pdf <http://www.biopsychiatry.com/pramipexole-mirapex.pdf> (retrieved 51012).

Moore et al. "An Efficient and Operationally Convenient General Synthesis of Tertiary Amines by Direct Alkylation of Secondary Amines with Alkyl Halides in the Presence of Huenig's Base" 2005, ARKIVOC 6:287-292.

Nagai et al., "Rats Expressing Human Cytosolic Copper-Zinc Superoxide Dismutase Transgenes with Amyotrophic Lateral Sclerosis: Associated Mutations Develop Motor Neuron Disease," Dec. 1, 201, The Journal of Neuroscience, 21(23): 9246-9254.

National Institutes of Health/ U.S. National Library of Medicine, "Creatine phosphokinase test", Updated Jan. 9, 2015, URL of this page: //www.nlm.nih.gov/medlineplus/ency/article/003503.htm, pp. 1-4.

Nilsen et al. "Mitochondria as Therapeutic Targets of Estrogen Action in the Central Nervous System" Aug. 2004, Curr. Drug Targets—CNS & Neurol. Disorders 3(4):297-313.

Ong et al. "An Evaluation of the Use of Two-Dimensional Gel Electrophoresis in Proteomics" 2001, Biomolecular Engineering 18(5):195-205.

Palliative (n.d.) The American Heritage.RTM. Stedman's Medical Dictionary, Retrieved Jun. 12, 2009, from Dictionary.com website: http://dictionary.com/browse/palliative.

Paquet et al. "The neuroendocrine precursor 7B2 is a sulfated protein proteolytically processed by a ubiquitous furin-like convertase" Jul. 29, 1994, J. Biol. Chem. 269(30):19279-19285.

Pattee et al. "Reduction of oxidative stress in amyotrophic lateral sclerosis following pramipexole treatment" Jan. 2003, Amyotrophic Lateral Sclerosis and Other Motor Neuron Disorders 4(2):90-95 (abstract only).

Paulson "Protein Fate in Neurodegenerative Proteinopathies: Polyglutamine Diseases Join the (Mis) Fold" 1999, Am. J. Hum. Genet. 64(2):339-345.

Petersen et al., Impaired Mitochondria Activity in the Insulin-Resistant Offspring of Patients with Type 2 Diabetes, 2004, New England Journal of Medicine 350:664-671.

Piercey et al. "Excitation of type II anterior caudate neurons by stimulation of dopamine $D_3$ receptors" 1997, Brain Research 762:19-28.

Piercey et al. "Inhibition of dopamine neuron firing by pramipexole, a dopamine $D_3$ receptor-prefering agonist: comparison to other dopamine receptor agonists" 1996, European J. of Pharmac. 312:35-44.

Public Statement on Mirapex, Sudden Onset of Sleep from the European Agency for the Evaluation of Medicinal Products (EMEA) , Jul. 19, 1999, www.emea.europa.eu/pdfs/human/press/pus/2064299.pdf.

Ranganathan et al, "Proteomic profiling of cerebrospinal fluid identifies biomarkers for amyotrophic lateral sclerosis" 2005, J Neurochem. 29:1461-1471.

Robberecht "Oxidative Stress in Amyotrophic Lateral Sclerosis" 2000, J. Neurol. 247(1):11-16 (abstract only).

Roca-Santiago et al. "Alzheimer's Disease and Age-related Macular Degeneration" Feb. 2006, Arch. Soc. Esp. Oftalmol. 81 (2):73-78.

(56) References Cited

OTHER PUBLICATIONS

Rothstein et al. "Beta-Lactam antibiotics offer neuroprotection by increasing glutamate transporter expression" 2005, Nature 433(7021):73-77.
Rowland et al. "Amyotrophic Lateral Sclerosis" May 2001, N Eng Journal of Medicine, 344:1688-1700.
Rudnicki et al., "Dexpramipexole effects on functional decline and survival in subjects with amyotrophic lateral sclerosis in a Phase II study: Subgroup analysis of demographic and clinical characteristics", Feb. 1, 2013, Amyotrophic LateralSclerosis and Frontotemporal Degeneration, vol. 14, pp. 44-51.
Ryberg et al. "Discovery and Verification of Amyotrophic Lateral Sclerosis Biomarkers by Proteomics" Jul. 2010, Muscle & Nerve 42(1):104-111.
Samson et al. "Long-Term Outcomes of 118 Patients with Eosinophilic Granulomatosis with Polyangiitis (Churge-Strauss Syndrome) Enrolled in Two Prospective Trials" 2013, J. of Autoimmunity 43:60-69.
Sanchez et al. "Cystatin C as a potential cerebrospinal fluid marker for the diagnosis of Creutzfeldt-Jakob disease" 2004, Proteomics 4(8):2229-2233.
Sayeed et al. "Patch Clamp Reveals Powerful Blockade of the Mitochondrial Permeability Transition Pore by the D2-Receptor Agonist Pramipexole" 2006, FASB Journal 20:556-558.
Schilling et al. "Neuroendocrine and side effect profile of pramipexole, a new dopamine receptor agonist, in humans" 1992, Clin. Pharmacol. Ther. 51:541-548.
Schmidt et al. "Neurodegenerative diseases of the retina and potential for protection and recovery" Jun. 2008 (printed from http://www.nncbi.nim.nih.gov/pubmed/19305795?dopt.sub.—Abstract) Curr. Neuropharmacol. 6(2) (Abstract only).
European Search Report and Opinion dated Aug. 2, 2012 for EP 12164060.
European Search Report and Opinion dated May 10, 2012 for EP 11186875.
European Search Report and Written Opinion dated Feb. 18, 2011 for EP 10009931.
European Search Report dated Mar. 2, 2011 for EP 10075571.9.
European Supplemental Search Report dated Apr. 8, 2010 for EP 08743922.
European Supplemental Search Report dated Apr. 9, 2010 for EP 08732306.9.
European Supplemental Search Report dated Nov. 23, 2006 for EP02795869.
European Supplemental Search Report dated Oct. 4, 2010 for EP 10008579.4.
Extended European Search Report and Written Opinion dated Sep. 11, 2012 for EP 12164067.
Extended European Supplemental Search Report and Written Opinion dated Feb. 18, 2011 for EP10075571.
Feher et al. "Mitochondrial alternations of retinal pigment epithelium in age—related macular degenteration" Jun. 2006, Neurobiology of Aging 27(7) (Abstract, 2 pages) (Printed from http//www.neurobiologyofaging.org/article/PIIS01974580005001545 on Dec. 11, 2009).
Ferger et al. "The dopamine agonist pramipexole scavenges hydroxyl free radicals induced by striatal application of 6-hydroxydopamine in rats: an in vivo microdialysis study" Aug. 29, 2000, Brain Research 883:216-223.
Golebiewski et al. "Application of GC/MS for Identyfication of the Sideproducts in a Process of Preparation of Pramipexole" May 16, 2006, Book of Abstracts: The Fifth Multidisciplinary conference on Drug Research, Pielaszek Research (Warszawa, Poland) Poster No. 1-57, p. 49.
Goodall et al. "Association of the H63D polymorphism in the hemochromatosis gene with sporadic ALS" 2005, Neurology 65(6):934-937.
Goodman et al. "The Pharmaceutical Basis of Therapeutics, 6.sup.th Ed." 1980, MacMillan Publishing Co., New York (TOC).

Gu et al., Pramipexole protects against apoptotic cell death by non-dopaminergic mechanisms, 2004, J. Neurochem. 91:1075-1081.
Guillevin et al. "Prognostic Factors in Polyarteritis Nodosa and Churg-Strauss Syndrome: A Prospective Study in 342 Patients" 1996, Medicine 75(1):17-28.
Gurney et al. "Motor Neuron Degeneration in Mice That Express a Human Cu, Zn Superoxide Dismutase Mutation" 1994, Science 264:1772-1775.
Haghikia et al. "Therapies for multiple sclerosis: translation achievements and outstanding needs" May 2013 Trends in Moleecular Medicine 19(5):309-319.
Halestrap "The Role of Mitochondria in Cell Death" Mar. 24, 2003, Endocrine Abstracts 5:513 (Abstract).
Hall et al. "Brain hydroxyl radical generation in acute experimental head injury" Feb. 1993, J. Neurochem. 60(2):588-594.
Hall et al. "Neuroprotective effects of the dopamine $D.sub.2 / D.sub.3$ agonist pramipexole against postischemic or methamphetamine-induced degeneration of nigrostriatal neurons" Aug. 6, 1996, Brain Research 742:80-88.
Hansen et al. "First Generation Process for the Preparation of the DPP-IV Inhibitor Sitagliptin" 2005, Organic Proc. Res. & Dev. 9:634-639.
Hardy et al. "Genetic Classification of Primary Neurodegenerative Disease" Nov. 6, 1998, Science 282 (5391)1075-1079.
Hasegawa et al. "A New Process for Synthesis of the Astrcyte Activation Suppressor, ONO-2506" 2005, Organic Proc. Res. & Dev. 9:774-781.
Hubble Pre-clinical Studies of Pramipexole: Clinical Relevance May 2000 Eur. J. Neurol. 7(Supp 1):15-20 (abstract only).
Initial Scientific Discussion for the Approval of Mirapex from the European Agency for the Evaluation of Medicinal Products (EMEA) 2005 www.emea.europa.eu/humandocs/PDFS/EPAR/Mirapexin/059097en6.pdf.
International Search Report and Written Opinion for PCT/US2006/031831 dated Dec. 7, 2006.
International Search Report and Written Opinion for PCT/US2007/087639 dated Apr. 7, 2007.
International Search Report and Written Opinion for PCT/US2008/057059 dated Jul. 11, 2008.
International Search Report and Written Opinion for PCT/US2008/057158 dated Jun. 29, 2009.
International Search Report and Written Opinion for PCT/US2009/054292 dated Oct. 22, 2009.
International Search Report and Written Opinion for PCT/US2010/039379 dated Aug. 25, 2010.
International Search Report and Written Opinion for PCT/US2011/038159 dated Dec. 12, 2011.
International Search Report and Written Opinion for PCT/US2013/054804 dated Mar. 21, 2014.
International Search Report and Written Opinion for PCT/US2014/019668 dated Jun. 9, 2014.
International Search Report and Written Opinion for PCT/US2014/046380 dated Dec. 10, 2014.
International Search Report and Written Opinion for PCT/US2014/050943 dated Nov. 6, 2014.
International Search Report and Written Opinion for PCT/US2014/050951 dated Oct. 22, 2014.
International Search Report and Written Opinion for PCT/US2016/022067 dated Jun. 3, 2016.
International Search Report for PCT/US2002/039970 dated Jul. 17, 2003.
Jacques et al. "Enantiomers, Racemates and Resolutions" 1981, John Wiley and Sons, Inc., New York (TOC).
Johnson et al. "Relationships between drug activity and NCI preclinical in vitro and in vivo models and early clinical trials" 2001, British Journal of Cancer 84(10):1424-1431.
Kato et al. "A neurosphere-derived factor, cystatin C, supports differentiation of ES cells into neural stem cells" 2006, PNAS USA 103(15):6019-6024.
Khan et al. "Alzheimer's disease cybrids replicate beta-amyloid abnormalities through cell death pathways" Aug. 2000, Ann Neurol. 48(2):148-55.

(56) References Cited

OTHER PUBLICATIONS

Kieburtz "Safety and Efficacy of Pramipexole in Early Parkinson Disease" 1997, JAMA 278(2):125-130.

Kitamura et al. "Protective Effects of the Antiparkinsonian Drugs Talipexole and Pramipexole against 1-Methyl-4-phenylpyridinium-Induced Apoptotic Death in Human Neuroblastoma SH-Sy5Y Cells" 1998, Molecular Pharmacology 54:1046-1054.

Lahortiga et al. "Activity of imatinib in systemic mastocytosis with chronic basophilic leukemia and a PRKG2-PDGFRB fusion" 2008, Haematological/The Hematology Journal 93(1): 51-56.

Le et al. "Antioxidant property of pramipexole independent of dopamine receptor activation in neuroprotection" 2000, J. Neural. Transm. 107(10):1165-73.

Lee et al. "Carcinogenicity Predictions for a Group of 30 Chemicals Undergoing Rodent Cancer Bioassays Based on Rules Derived from Subchronic Organ Toxicities" 1996, Environmental Health Perspectives 104(5):1059-1063.

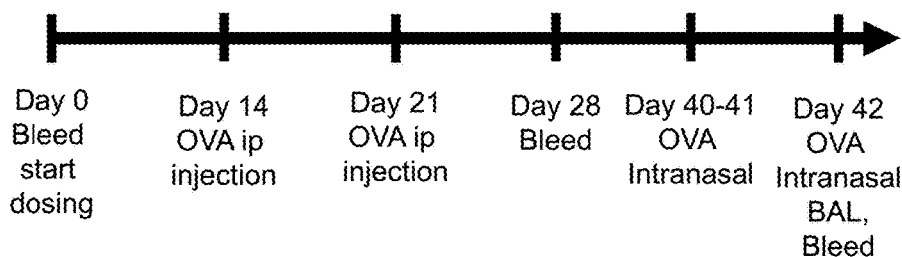
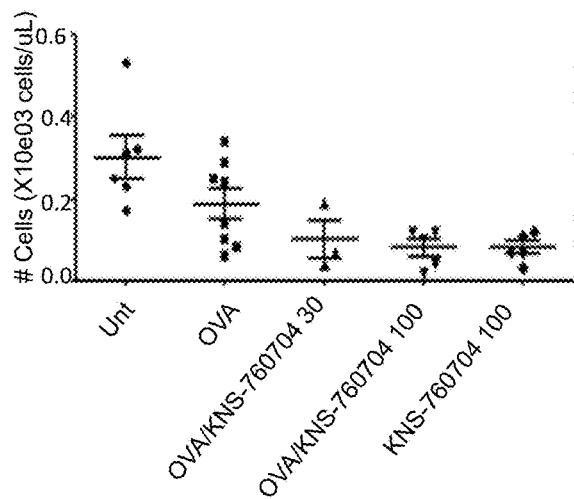
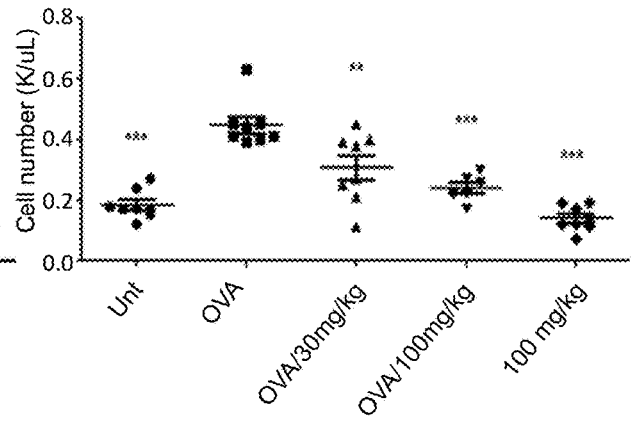
FIG. 7

| Description, n (%) | Dexpramipexole* (N=474) | Placebo (N=468) |
|---|---|---|
| ANC <2 x 10⁹/L (neutropenia) | 76 (16) | 35 (7) |
| Grade 1: ≥1.5 - <2 x 10⁹/L | 47 (10) | 27 (6) |
| Grade 2: ≥1.0 - <1.5 x 10⁹/L | 13 (3) | 7 (1) |
| Grade 3: ≥0.5 - <1.0 x 10⁹/L | 5 (1) | 0 |
| Grade 4: <0.5 x 10⁹/L | 11 (2) | 1 (<1) |
| > 1 episode of neutropenia | 15 (3) | 2 (<1) |
| Resolution of neutropenia after holding/stopping study treatment | 19 (4) | 1 (<1) |
| Restarted study treatment after neutropenia | 15 (3) | 0 |
| Neutropenia recurrence after restarting study treatment | 8 (2) | 0 |
| Mean duration (±SD) of neutropenia, days | 19.7 (±20.2) | 12.5 (±7.5) |

FIG. 9

COMPOSITIONS AND METHODS FOR TREATING CONDITIONS RELATED TO INCREASED EOSINOPHILS

CROSS-REFERENCE TO RELATED APPLICATIONS

This application is a continuation of U.S. application Ser. No. 13/966,229 entitled "Compositions And Methods For Treating Conditions Related To Increased Eosinophils", filed Aug. 13, 2013 which claims the benefit of U.S. Provisional Application No. 61/845,944 entitled "Compositions and Methods for Treating Conditions Related to Increased Eosinophils" filed Jul. 12, 2013, U.S. Provisional Application No. 61/859,158 entitled "Compositions and Methods for Treating Conditions Related to Increased Eosinophils" filed Jul. 26, 2013, and U.S. Provisional Application No. 61/865,118 entitled "Compositions and Methods for Treating Conditions Related to Increased Eosinophils" filed Aug. 12, 2013, each of which are hereby incorporated herein by reference in their entirety.

SUMMARY

Disclosed herein are methods for the treatment of diseases associated with pathogenic or elevated levels of eosinophils, neutrophils or basophils with R(+) pramipexole or a pharmaceutically acceptable salt thereof.

Embodiments herein are directed to methods of treating a condition characterized by increased numbers of eosinophils in a subject comprising administering to a subject in need thereof a therapeutically effective amount of R(+) pramipexole or a pharmaceutically acceptable salt thereof.

In some embodiments, the condition is selected from incomplete Kawasaki disease (iKd), Behcet Disease, tonsolitis and cervical adenitis, Graves' ophthalmology, Churg Strauss, nasal polyposis, atopic dermatitis, eosinophilic esophagitis, hypereosinophilic syndrome, asthma, allergic rhinitis, non-allergic rhinitis with eosinophilia syndrome, eosinophilic granuloma (histiocytosis X), eosinophilic polymyositis, chronic eosinophilic pneumonia, eosinophilic gastroenteritis, aggressive systemic mastocytosis, Gleich's syndrome, eosinophilia myalgia syndrome, Omenn syndrome, hyper-IgE syndrome, eosinophilic leukemia, and inflammatory bowel diseases. In some embodiments, the condition is hypereosinophilic syndrome. In some embodiments, the condition is an inflammatory condition. In some embodiments, the condition characterized by increased numbers of eosinophils is characterized by eosinophil numbers above about 450 cells per microliter in the peripheral blood.

In some embodiments, the therapeutically effective amount is from about 50 mg to about 1,500 mg per day. In some embodiments, the therapeutically effective amount is from about 150 mg to about 1,500 mg per day. In some embodiments, the therapeutically effective amount is from about 150 mg to about 300 mg per day.

In some embodiments, administering comprises administering a fraction of the daily dose two or more times per day. In some embodiments, administering comprises administering a dose equal to about half of a daily dose twice per day. In some embodiments, the dose is administered every 12 hours. In some embodiments, administering comprises administering about 150 mg two times per day.

Some embodiments further comprise monitoring the patient. Some embodiments further comprise monitoring the patient for neutropenia.

Some embodiments further comprise an induction step. In some embodiments, said induction step comprises administering a second therapeutic agent other than R(+) pramipexole that is capable of decreasing eosinophil levels. In some embodiments, said induction step is from about 1 week to about 6 months.

Some embodiments are directed to methods of treating a condition characterized by increased numbers of basophils in a subject comprising administering to a subject in need thereof a therapeutically effective amount of R(+) pramipexole or a pharmaceutically acceptable salt thereof.

In some embodiments, the condition is selected from allergy, and herpes stromal keratitis. In some embodiments, the condition is an inflammatory condition. In some embodiments, the condition characterized by increased numbers of basophils is characterized by eosinophil numbers above about 200 cells per microliter in the peripheral blood.

In some embodiments, the therapeutically effective amount is from about 50 mg to about 1,500 mg per day. In some embodiments, the therapeutically effective amount is from about 150 mg to about 1,500 mg per day. In some embodiments, the therapeutically effective amount is from about 150 mg to about 300 mg per day.

In some embodiments, administering comprises administering a fraction of the daily dose two or more times per day. In some embodiments, administering comprises administering a dose equal to about half of a daily dose twice per day. In some embodiments, the dose is administered every 12 hours. In some embodiments, administering comprises administering about 150 mg two times per day.

Some embodiments further comprise monitoring the patient. Some embodiments further comprise monitoring the patient for neutropenia.

Some embodiments further comprise an induction step. In some embodiments, said induction step comprises administering a second therapeutic agent that is capable of decreasing eosinophil levels. In some embodiments, said induction step is from about 1 week to about 6 months.

Some embodiments are directed to methods of treating a condition characterized by increased numbers of neutrophils in a subject comprising: administering to a subject in need thereof a therapeutically effective amount of R(+) pramipexole or a pharmaceutically acceptable salt thereof.

In some embodiments, the condition is selected from drug induced injuries, cutaneous reactions and disorders including bullous pemphigoid, chronic granulomatous disease, vasculitides including Wegener's and ANCA-associated vasculitis, intracerebral hemorrhage, spinal cord injury, traumatic brain injury, multiple sclerosis, neuromyelitis optica, immune-mediated neurologic disorders, inflammatory bowel disease, respiratory disorders including asthma and COPD, autoimmune disorders including IDDM and SLE and rheumatoid arthritis, non-insulin dependent diabetes, herpes stromal keratitis and neurodegenerative diseases. In some embodiments, the condition is an inflammatory condition. In some embodiments, the condition characterized by increased numbers of neutrophils is characterized by neutrophil numbers above about 7,700 cells per microliter in the peripheral blood.

In some embodiments, the therapeutically effective amount is from about 50 mg to about 1,500 mg per day. In some embodiments, the therapeutically effective amount is from about 150 mg to about 1,500 mg per day. In some embodiments, the therapeutically effective amount is from about 150 mg to about 300 mg per day.

In some embodiments, administering comprises administering a fraction of the daily dose two or more times per day.

In some embodiments, administering comprises administering a dose equal to about half of a daily dose twice per day. In some embodiments, the dose is administered every 12 hours. In some embodiments, administering comprises administering about 150 mg two times per day.

Some embodiments further comprise monitoring the patient. Some embodiments further comprise monitoring the patient for neutropenia.

Some embodiments further comprise an induction step. In some embodiments, said induction step comprises administering a therapeutic agent that is capable of decreasing eosinophil levels. In some embodiments, said induction step is from about 1 week to about 6 months.

BRIEF DESCRIPTION OF THE DRAWINGS

FIG. 7 depicts the effects of R(+) pramipexole in an ovalabumin pulmonary inflammation mouse model.

FIG. 9 shows that as with the Phase II study, a low incidence of neutropenia in the dexpramipexole treated group was observed which resolved upon dexpramipexole withdrawal.

DETAILED DESCRIPTION

Figure 1:
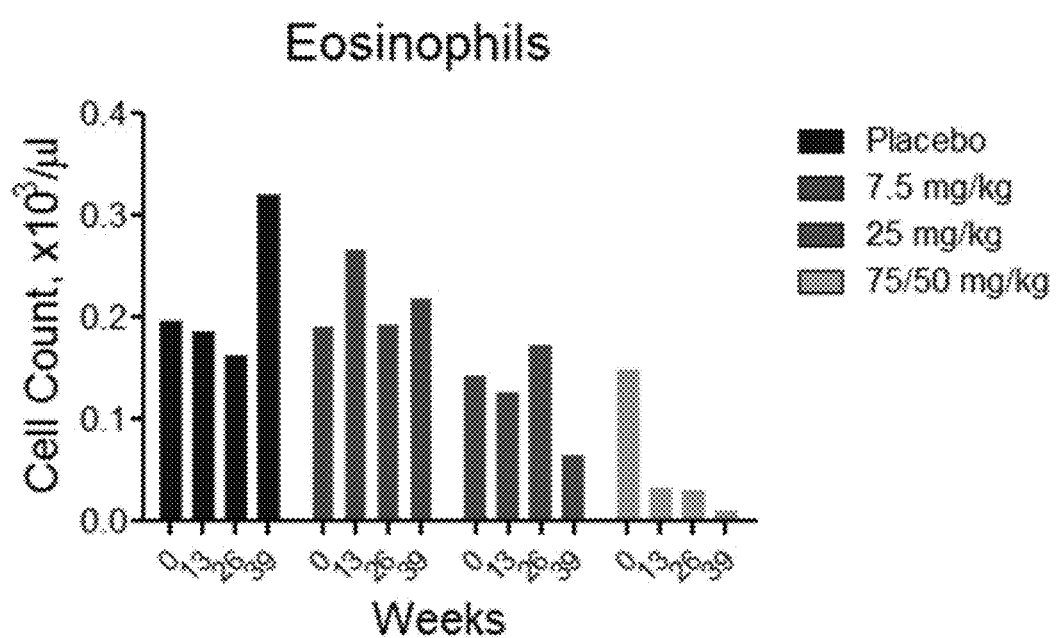
FIG. 1 depicts the dose- and time-dependent effects of R(+) pramipexole on eosinophil counts in minipigs. The reduction of eosinophils was observed in minipigs in long-term toxicity studies (n=3-5 per group).

Dexpramipexole ((6R)-2-amino-4,5,6,7-tetrahydro-6-(propylamino)benzothiazole), also referred to as "R(+) pramipexole", is a synthetic aminobenzothiazole derivative. The (6S) enantiomer of dexpramipexole, commonly known as pramipexole and commercially available under the MIRAPEX® name, is a potent dopamine agonist, which mimics the effects of the neurotransmitter dopamine. Pramipexole has also been shown to have neuroprotective in addition to dopaminergic activities, presumably through inhibition of lipid peroxidation, normalization of mitochondrial metabolism and/or detoxification of oxygen radicals. Therefore, pramipexole may have utility as an inhibitor of the cell death cascades and loss of cell viability observed in neurodegenerative diseases such as Parkinson's disease. Additionally, oxidative stress caused by an increase in oxygen and other free radicals has been associated with the fatal neurodegenerative disorder amyotrophic lateral sclerosis, a progressive neurodegenerative disorder involving the motor neurons of the cortex, brain stem, and spinal cord.

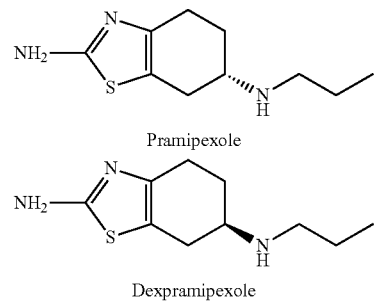

Pramipexole

Dexpramipexole

The neuroprotectant activity of both enantiomers are expected to require therapeutic doses in the range of about 100 mg/day to about 1,500 mg/day or more, however pramipexole's agonistic effect on the D2 family of dopamine receptors only allows therapeutic doses that range between 0.5 and 5.0 mg/day. However, even at these low doses, significant adverse side effects have been reported. For example, the Boehringer Ingelheim product insert for pramipexole sets the maximally tolerated dose for humans at 4.5 mg/day, and a dose of pramipexole as low as 1.5 mg has been shown to cause somnolence in humans. Single dose toxicity of pramipexole after oral administration has been studied in rodents, dogs, monkeys and humans. In rodents, death occurred at doses of 70-105 mg/kg and above which is equivalent to a human dose of 7-12 mg/kg or approximately 500-850 mg for a 70 kg (~150 lb) individual. In dogs, vomiting occurred at 0.0007 mg/kg and above, while monkeys displayed major excitation at 3.5 mg/kg. In human subjects, an initial single dose of pramipexole of greater than 0.20 mg was not tolerated. All species showed signs of toxicity related to exaggerated pharmacodynamic responses to the dopaminergic agonism of pramipexole.

Although any methods and materials similar or equivalent to those described herein can be used in the practice or testing of embodiments of the present invention, the preferred methods, devices, and materials are now described.

In each of the embodiments disclosed herein, the compounds and methods can be utilized with or on a subject in need of such treatment, which can also be referred to as "in need thereof" As used herein, the phrase "in need thereof" means that the subject has been identified as having a need for the particular method or treatment and that the treatment has been given to the subject for that particular purpose."

The term "patient" and "subject" are interchangeable and may be taken to mean any living organism which may be treated with compounds of the present invention. As such, the terms "patient" and "subject" may include, but is not limited to, any non-human mammal, primate or human. In some embodiments, the "patient" or "subject" is a mammal, such as mice, rats, other rodents, rabbits, dogs, cats, swine, cattle, sheep, horses, primates, or humans. In some embodiments, the patient or subject is an adult, child or infant. In some embodiments, the patient or subject is a human.

Various embodiments described herein are directed to a method of treating a condition characterized by pathogenic basophils, eosinophils and/or neutrophils in a patient comprising administering to the patient a therapeutically effective amount of (6R)-2-amino-4,5,6,7-tetrahydro-6-(propylamino)benzothiazole, or a pharmaceutically acceptable salt thereof. In some embodiments, the condition is characterized by increased levels of basophils, eosinophils and/or neutrophils.

Various embodiments described herein are directed to a method of treating a condition characterized by pathogenic basophils, eosinophils or neutrophils in a patient comprising administering to the patient a pharmaceutical composition comprising a therapeutically effective amount of (6R)-2-amino-4,5,6,7-tetrahydro-6-(propylamino)benzothiazole, or a pharmaceutically acceptable salt thereof. In some embodiments, the condition is characterized by increased levels of basophils, eosinophils and/or neutrophils.

In some embodiments, the condition is an allergic condition. In still other embodiments, the condition is an inflammatory condition. In some embodiments, the condition is selected from the group consisting of Incomplete Kawasaki disease (iKd), Behcet Disease, tonsolitis and cervical adenitis, Graves' ophthalmology, chronic eosinophilic pneumonia, eosinophilic gastroenteritis, aggressive systemic mastocytosis, Gleich's syndrome, eosinophilia myalgia syndrome, Omenn syndrome, hyper-IgE syndrome, Churg Strauss syndrome, nasal polyposis, atopic dermatitis, eosinophilic esophagitis, hypereosinophilic syndromes, allergic rhinitis, non-allergic rhinitis with eosinophilia syndrome, eosinophilic granuloma (histiocytosis X), eosinophilic polymyositis, allergy, drug induced injuries, cutaneous reactions and disorders including bullous pemphigoid, chronic granulomatous disease, vasculitides including Wegener's and ANCA-associated vasculitis, intracerebral hemorrhage, spinal cord injury, traumatic brain injury, multiple sclerosis and other neuroinflammatory diseases, neuromyelitis optica, herpes stromal keratitis, immune-mediated neurologic disorders, microglia-derived inflammation, inflammatory bowel disease, respiratory disorders including asthma and COPD, autoimmune disorders including insulin dependent diabetes mellitus, systemic lupus erythematosus and rheumatoid arthritis, non-insulin dependent diabetes, dermatitis herpetiformis, parasitic infections, malaria-induced cerebellar damage, Hodgkin's lymphoma, Non-Hodgkin lymphoma, systemic authoimmune diseases, cholesterol embolism, coccidioidomycosis, ovarian cancer, and neurodegenerative disease.

In some embodiments, the condition is characterized by pathogenic eosinophils or elevated eosinophil levels. In some embodiments, the condition is selected from the group consisting of incomplete Kawasaki disease (iKd), Behcet Disease, tonsolitis and cervical adenitis, Graves' ophthalmology, Churg Strauss, nasal polyposis, atopic dermatitis, eosinophilic esophagitis, hypereosinophilic syndrome, asthma, allergic rhinitis, non-allergic rhinitis with eosinophilia syndrome, eosinophilic granuloma (histiocytosis X), eosinophilic polymyositis, chronic eosinophilic pneumonia, eosinophilic gastroenteritis, aggressive systemic mastocytosis, Gleich's syndrome, eosinophilia myalgia syndrome, Omenn syndrome, hyper-IgE syndrome, as eosinophilic leukemia, and inflammatory bowel diseases.

In some embodiments, the condition is characterized by pathogenic basophils or elevated basophil levels. In some embodiments, the condition is selected from the group consisting of allergy, and herpes stromal keratitis.

In some embodiments, the condition is characterized by pathogenic neutrophils or elevated neutrophil levels. In some embodiments, the condition is selected from the group consisting of drug induced injuries, cutaneous reactions and disorders including bullous pemphigoid, chronic granulomatous disease, vasculitides including Wegener's and ANCA-associated vasculitis, intracerebral hemorrhage, spinal cord injury, traumatic brain injury, multiple sclerosis, neuromyelitis optica, immune-mediated neurologic disorders, inflammatory bowel disease, respiratory disorders including asthma and COPD, autoimmune disorders including IDDM and SLE and rheumatoid arthritis, non-insulin dependent diabetes, herpes stromal keratitis and neurodegenerative diseases.

In some embodiments, the condition is not a neurodegenerative disease. In some embodiments, the condition is not Parkinson's disease, Alzheimer's disease or amyotrophic lateral sclerosis.

In some embodiments, the condition is an inflammatory condition. Inflammation symptoms can be associated with a large, unrelated group of disorders which underlay a variety of diseases and disorders. The immune system is often involved with inflammatory disorders, demonstrated in both allergic reactions and some myopathies, with many immune system disorders resulting in abnormal inflammation. Non-immune diseases with etiological origins in inflammatory processes include cancer, atherosclerosis, and ischaemic heart disease. Non-limiting examples of disorders exhibiting inflammation as a symptom include, without limitation, acne, acid reflux/heartburn, age related macular degeneration (AMD), allergy, allergic rhinitis, Alzheimer's disease, amyotrophic lateral sclerosis, anemia, appendicitis, arteritis, arthritis, asthma, atherosclerosis, autoimmune disorders, balanitis, blepharitis, bronchiolitis, bronchitis, a bullous pemphigoid, burn, bursitis, cancer, cardiac arrest, carditis, celiac disease, cellulitis, cervicitis, cholangitis, cholecystitis, chorioamnionitis, chronic obstructive pulmonary disease (COPD), cirrhosis, colitis, congestive heart failure, conjunctivitis, cyclophosphamide-induced cystitis, cystic fibrosis, cystitis, common cold, dacryoadenitis, dementia, dermatitis, dermatomyositis, diabetes, diabetic neuropathy, diabetic retinopathy, diabetic nephropathy, diabetic ulcer, digestive system disease, eczema, emphysema, encephalitis, endocarditis, endometritis, enteritis, enterocolitis, epicondylitis, epididymitis, fasciitis, fibromyalgia, fibrosis, fibrositis, gastritis, gastroenteritis, gingivitis, glomerulonephritis, glossitis, heart disease, heart valve dysfunction, hepatitis, hidradenitis suppurativa, Huntington's disease, hyperlipidemic pancreatitis, hypertension, ileitis, infection, inflammatory bowel disease, inflammatory cardiomegaly, inflammatory neuropathy, insulin resistance, interstitial cystitis, interstitial nephritis, iritis, ischemia, ischemic heart disease, keratitis, keratoconjunctivitis, laryngitis, lupus nephritis, mastitis, mastoiditis, meningitis, metabolic syndrome (syndrome X), a migraine, multiple sclerosis and other neuroinflammatory diseases, myelitis, myocarditis, myositis, nephritis, non-alcoholic steatohepatitis, obesity, omphalitis, oophoritis, orchitis, osteochondritis, osteopenia, osteomyelitis, osteoporosis, osteitis, otitis, pancreatitis, Parkinson's disease, parotitis, pelvic inflammatory disease, pemphigus vularis, pericarditis, peritonitis, pharyngitis, phlebitis, pleuritis, pneumonitis, polycystic nephritis, proctitis, prostatitis, psoriasis, pulpitis, pyelonephritis, pylephlebitis, renal failure, reperfusion injury, retinitis, rheumatic fever, rhinitis, salpingitis, sarcoidosis, sialadenitis, sinusitis, spastic colon, stenosis, stomatitis, stroke, surgical complication, synovitis, tendonitis, tendinosis, tenosynovitis, thrombophlebitis, tonsillitis, trauma, traumatic brain injury, transplant rejection, trigonitis, tuberculosis, tumor, urethritis, ursitis, uveitis, vaginitis, vasculitis, and vulvitis. In another embodiment, the inflammation comprises a systemic inflammation. Systemic inflammation is not confined to a particular tissue may overwhelm the body, and involve the endothelium and other organ systems. When it is due to infection, the term sepsis is applied, with the terms bacteremia being applied specifically for bacterial sepsis and viremia specifically to viral sepsis. Vasodilation and organ dysfunction are serious problems associated with widespread infection that may lead to septic shock and death. In another embodiment, the inflammation comprises an arthritis. Arthritis includes a group of conditions involving damage to the joints of the body due to the inflammation of the synovium including, without limitation osteoarthritis, rheumatoid arthritis, juvenile idiopathic arthritis, spondyloarthropathies like ankylosing spondylitis, reactive arthritis (Reiter's syndrome), psoriatic arthritis, enteropathic arthritis associated with inflammatory bowel disease, Whipple disease and Behcet disease, septic arthritis, gout (also known as gouty arthritis, crystal synovitis, metabolic arthritis), pseudogout (calcium pyrophosphate deposition disease), and Still's disease. Arthritis can affect a single joint (monoarthritis), two to four joints (oligoarthritis) or five or more joints (polyarthritis) and can be either an auto-immune disease or a non-autoimmune disease.

In some embodiments, the condition is characterized by pathogenic basophils, eosinophils and/or neutrophils in the systemic circulation. In some embodiments, the condition is characterized by pathogenic basophils, eosinophils or neutrophils in tissue. In some embodiments, the condition is characterized by pathogenic basophils, eosinophils or neutrophils in tissues including, but not limited to the lung tissue, bone marrow, heart tissue, or nasal passage tissue. In some embodiments, the condition is characterized by increased levels of basophils, eosinophils or neutrophils in the systemic circulation. In some embodiments, the condition is characterized by increased levels of basophils, eosinophils, or neutrophils in the tissues. In yet other embodiments, the condition is characterized by increased levels of basophils, eosinophils or neutrophils in the systemic circulation and tissues. In some embodiments, the condition is characterized by increased levels of basophils, eosinophils or neutrophils in tissues including, but not limited to the lung tissue, bone marrow, heart tissue, or nasal passage tissue.

In some embodiments, treating the condition results in a decrease in the numbers of basophils, eosinophils or neutrophils in the circulation, tissue, or a combination thereof. In yet another preferred embodiment, treating the condition results in a decrease in the numbers of basophils, eosinophils or neutrophils in the circulation and tissues. In preferred embodiments, treating the condition results in a decrease in the numbers of basophils, eosinophils or neutrophils in the tissues. In yet another preferred embodiment treating the condition results in a decrease in the numbers of basophils, eosinophils or neutrophils in tissues including, but not limited to the lung tissue, bone marrow, heart tissue, or nasal passage tissue.

As used herein, a condition characterized by increased numbers of eosinophils, neutrophils and/or basophils in a subject refers to a condition in which the numbers of eosinophils, neutrophils and/or basophils, as the case may be, are increased or elevated compared with a normal subject.

In some embodiments, a normal subject is one that has eosinophil levels of less than about 350 cells per microliter in the peripheral blood. In some embodiments, a condition characterized by increased levels of eosinophils is characterized by eosinophil levels above about 450 cells per microliter in the peripheral blood. In yet other embodiments a condition characterized by increased levels of eosinophils is characterized by eosinophil levels selected from above about 250 cells per microliter in the peripheral blood, 350 cells per microliter in the peripheral blood, 450 cells per microliter in the peripheral blood, 500 cells per microliter in the peripheral blood, 600 cells per microliter in the peripheral blood, 700 cells per microliter in the peripheral blood, 800 cells per microliter in the peripheral blood, 900 cells per microliter in the peripheral blood, 1,000 cells per microliter in the peripheral blood, 1,100 cells per microliter in the peripheral blood, 1,200 cells per microliter in the peripheral blood, 1,300 cells per microliter in the peripheral blood, 1,400 cells per microliter in the peripheral blood, and 1,500 cells per microliter in the peripheral blood. In some embodiments, the condition is hypereosinophilic syndrome, which is characterized by eosinophil levels above about 1,500 cells per microliter in the peripheral blood.

In some embodiments, a normal subject is one that has basophil levels of less than about 200 cells per microliter in the peripheral blood. In some embodiments, a condition characterized by increased levels of basophils is characterized by basophil levels selected from above about 200 cells per microliter in the peripheral blood, above about 300 cells per microliter in the peripheral blood, above about 400 cells per microliter in the peripheral blood, and above about 500 cells per microliter in the peripheral blood.

In some embodiments, a normal subject is one that has neutrophil levels of less than about 7,700 cells per microliter in the peripheral blood. In some embodiments a condition characterized by increased levels of neutrophils is characterized by neutrophil levels selected from above about 7,700 cells per microliter in the peripheral blood, above about 7,800 cells per microliter in the peripheral blood, above about 7,800 cells per microliter in the peripheral blood, above about 7,900 cells per microliter in the peripheral blood and above about 8,000 cells per microliter in the peripheral blood.

In some embodiments, treatment with a therapeutically effective amount of R(+) pramipexole may include administering daily doses of about 0.1 mg or more, about 1 mg or more, 10 mg or more, 100 mg or more, about 125 mg or more, about 150 mg or more, 300 mg or more, 400 mg or more, 450 mg or more, 500 mg or more, 600 mg or more, 700 mg or more, 800 mg or more or about 1,000 mg or more, about 1,200 mg or more or about 1,500 mg or more or more. In some embodiments, treatment with a therapeutically effective amount of R(+) pramipexole is without the adverse side effects associated with dopaminergic agonism.

In some embodiments, treatment with a therapeutically effective amount of R(+) pramipexole may include administering single unit doses of about 0.1 mg or more, about 1 mg or more, 10 mg or more, 100 mg or more, about 125 mg or more, about 150 mg or more, 300 mg or more, 400 mg or more, 450 mg or more, 500 mg or more, 600 mg or more, 700 mg or more, 800 mg or more or about 1,000 mg or more, about 1,200 mg or more or about 1,500 mg or more or more In some embodiments, treatment with a therapeutically effective amount of R(+) pramipexole is without the adverse side effects associated with dopaminergic agonism. In some embodiments, such single unit doses may be administered once per day or multiple times per day, such as twice per day or three times per day.

In some embodiments, treatment with a therapeutically effective amount of R(+) pramipexole may include administration for prolonged periods of time such as, for example, 12 weeks or more, 6 months or more, 1 year or more and, in certain embodiments, for 2, 3, 5 or 10 years or more, and in other embodiments, for an indefinite period of time. Accordingly, embodiments include methods of treating disease may include administering R(+) pramipexole for an extended or prolonged period of time. In some embodiments, the extended period of time may be about 12 weeks or longer, about 6 months or longer, about 1 year or longer, and in other embodiments, a method of treating disease comprises administering R(+) pramipexole on a maintenance dosing regimen. In such embodiments, the maintenance dosing regimen may include administering about 0.1 mg or more, about 1 mg or more, 10 mg or more, 100 mg or more, about 125 mg or more, about 150 mg or more, 300 mg or more, 400 mg or more, 450 mg or more, 500 mg or more, 600 mg or more, 700 mg or more, 800 mg or more or about 1,000 mg or more, about 1,200 mg or more or about 1,500 mg or more or more of R(+) pramipexole per day without any titration (or an initial dosing regimen of less than the maintenance dose). In some embodiments, the daily dose may be administered once per day or multiple times per day, such as twice per day or three times per day. Thus, various embodiments are directed to maintenance therapy in which a dosing schedule for R(+) pramipexole is maintained for an extended period of time without titration or otherwise changing the dosing schedule. In such embodiments, the extended period of time may be about 12 weeks or longer, about 6 months or longer, about 1 year or longer, 2, 3, 4, 5, or 10 years or longer, and in certain embodiments, an indefinite period of time.

Treatment including administration of single unit doses of about 0.1 mg or more, about 1 mg or more, about 10 mg or more, about 100 mg or more, about 125 mg or more, about 150 mg or more, about 300 mg or more, about 400 mg or more, about 450 mg or more, about 500 mg or more, about 600 mg or more, about 700 mg or more, about 800 mg or more or about 1,000 mg or more, about 1,200 mg or more or about 1,500 mg or more of R(+) pramipexole may be carried out for prolonged periods of time such as, for example, 12 weeks or more, 6 months or more, 1 year or more and, in certain embodiments, for 2, 3, 5 or 10 years or more, and in other embodiments, for an indefinite period of time.

In other embodiments, the maintenance therapy dosing may include administering less than the initial daily dose, such as, less than about 150 mg, or less than about 300 mg, or less than 600 mg of R(+) pramipexole per day. Additionally, without wishing to be bound by theory, the adverse effects associated with dopamine agonist treatment such as those described above may not develop after treatment with R(+) pramipexole has been carried out for a period of time of at least 12 weeks or more, and in some embodiments at least 6 months or 1, 2, 3, 5 or 10 years or more.

In further embodiments, an initial dosing regimen may be provided. In certain embodiments, the initial dosing regimen may include administering a higher dose of R(+) pramipexole than the maintenance dosing regimen as either a single administration or by administering an increased dosage for a limited period of time prior to beginning a maintenance dosing regimen. For example, in certain embodiments, the initial dosing regimen may be about 150 mg to about 300 mg or more of R(+) pramipexole, about 300 mg to about 500 mg or more of R(+) pramipexole per day, or from about 300 mg to about 600 mg or more of R(+) pramipexole per day, these initial dosing regimen may continue for 1, 2, 3, 4, 5, 6, or 7 days, up to 4 weeks, up to 8 weeks, or up to 12 weeks. Following the initial dosing regimen, the patient may be administered a maintenance dosing regimen of, for example, about 0.1 mg or more, about 1 mg or more, 10 mg or more, 100 mg or more, about 125 mg or more, about 150 mg or more, 300 mg or more, 400 mg or more, 450 mg or more, 500 mg or more, 600 mg or more, 700 mg or more, 800 mg or more or about 1,000 mg or more, about 1,200 mg or more or about 1,500 mg or more of R(+) pramipexole for an indefinite period of time such as, for example, at least 12 weeks or more or at least 6 months or 1, 2, 3, 5 or 10 years or more. In some embodiments, patients undergoing a maintenance regimen may be administered one or more higher dosage treatments at one or more times during the maintenance dosage regimen. Following the initial dosing regimen, the patient may be administered a maintenance dosing regimen of, for example, greater than 0.1 mg, greater than 1 mg, greater than 10 mg, greater than 100 mg, greater than 125 mg, greater than 150 mg, greater than 300 mg, greater than 400 mg, greater than 450 mg, greater than 500 mg, greater than 600 mg, greater than 700 mg, greater than 800 mg, greater than 1,000 mg, greater than 1,200 mg, or greater than 1,500 mg of R(+) pramipexole for an indefinite period of time such as, for example, at least 12 weeks or more or at least 6 months or 1, 2, 3, 5 or 10 years or more. In some embodiments, patients undergoing a maintenance regimen may be administered one or more higher dosage treatments at one or more times during the maintenance dosage regimen. Following the initial dosing regimen, the patient may be administered a maintenance dosing regimen of, for example, about 0.1 mg or more, about 1 mg or more, about 10 mg or more, about 100 mg or more, about 125 mg or more, about 150 mg or more, about 300 mg or more, about 400 mg or more, about 450 mg or more, about 500 mg or more, about 600 mg or more, about 700 mg or more, about 800 mg or more, about 1,000 mg or more, about 1,200 mg or more or about 1,500 mg or more of R(+) pramipexole for an indefinite period of time such as, for example, at least 12 weeks or more or at least 6 months or 1, 2, 3, 5 or 10 years or more. In some embodiments, patients undergoing a maintenance regimen may be administered one or more higher dosage treatments at one or more times during the maintenance dosage regimen.

Embodiments are also directed to a dosage regimen for administering R(+) pramipexole to treat the conditions disclosed herein. For example, in some embodiments, the dosage regimen may include an initial dose of R(+) pramipexole in one or more unit doses, then a plurality of daily doses having an equal amount of R(+) pramipexole as the initial dose in one or more unit doses. Such embodiments are not limited by the amount of the initial dose and daily doses. For example, in particular embodiments, the initial dose and each of the plurality of daily doses may be from about 50 mg to about 300 mg or about 400 mg, or about 450 mg, or about 500 mg or about 600 mg of R(+) pramipexole. In other embodiments, the initial dose and each of the plurality of daily doses may be from about 150 mg to about 300 mg or about 400 mg, or about 450 mg, or about 500 mg or about 600 mg of R(+) pramipexole. In other embodiments, the initial dose and each of the plurality of daily doses may be from about 0.1 mg or more, about 1 mg or more, 10 mg or more, 100 mg or more, about 125 mg or more, about 150 mg or more, 300 mg or more, 400 mg or more, 450 mg or more, 500 mg or more, 600 mg or more, 700 mg or more, 800 mg or more, about 1,000 mg or more, about 1,200 mg or more or about 1,500 mg or more of R(+) pramipexole, and in still other embodiments, the initial dose and each of the plurality of daily doses may be about 150 mg or more, may be about 300 mg or more, about 400 mg or more, or about 450 mg or more, or about 500 mg or more, or about 600 mg or more of R(+) pramipexole. In yet other embodiments, the initial dose and each of the plurality of daily doses may be greater than 0.1 mg, greater than 1 mg, greater than 10 mg, greater than 100 mg, greater than 125 mg, greater than 150 mg, greater than 300 mg, greater than 400 mg, greater than 450 mg, greater than 500 mg, greater than 600 mg, greater than 700 mg, greater than 800 mg, or greater than 1,000 mg, greater than 1,200 mg, or greater than 1,500 mg. In some embodiments, the one or more unit doses of the dosage regimen may be 1 to 5 unit doses, and in such embodiments, each of the one or more unit doses may be substantially equal. In some embodiments, the one or more unit doses of the dosage regimen may be about 150 mg, at least about 150 mg or greater than 150 mg of R(+) pramipexole. In some embodiments, two unit doses of about 150 mg are administered daily, wherein each unit dose may be substantially equal. In some embodiments, three unit doses of about 150 mg are administered daily, wherein each unit dose may be substantially equal. In some embodiments, the one or more unit doses of the dosage regimen may be about 300 mg, at least about 300 mg or greater than 300 mg of R(+) pramipexole. In some embodiments, two unit doses of 300 mg are administered daily, wherein each unit dose may be substantially equal. In other embodiments, each unit dose of the dosage regimen may be a solid unit dose. Each of the dosage regimens for R(+) pramipexole described herein may be used in any of the methods, and the dosing regimen may be carried out using any of the compositions described herein.

Various embodiments may also comprise an induction step comprising administration of a therapeutically effective amount of a therapeutic agent capable of decreasing eosinophil, basophil or neutrophil levels in the patient. In some embodiments, the therapeutic agent is not R(+) pramipexole. In some embodiments, the therapeutic agent is any drug that induces anti-inflammatory effects. In some embodiments, the therapeutic agent may be a glucocorticoid, a non-steroidal anti-inflammatory drug (NSAIDs), phenolic antioxidants, anti-proliferative drug, or a combination thereof. In some embodiments, anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, curcumin, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, lysofylline, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, mepolizumab, prodrugs thereof, and combinations thereof.

In some embodiments, the induction step comprises administering a therapeutically effective amount of the therapeutic agent for a period of about 1 to about 6 months. In some embodiments, the therapeutic agent is administered for a period of about 1 week, about 2 weeks, about 3 weeks, about 1 month, about 2 months, about 3 months or about 4 months, about 5 months or about 6 months. In some embodiments, induction step comprises administering a therapeutically effective amount of the therapeutic agent for a period of less than 1 week, about 1 to 2 weeks, about 2 to 3 weeks, about 3 to 4 weeks about 1 to 2 months, about 2 to 3 months, or about 3 to 4 months. In yet other embodiments, the induction step comprises administering a therapeutically effective amount of the therapeutic agent until a pre-determined eosinophil, basophil or neutrophil level is reached after which the induction step is discontinued, titrated out, or a combination thereof. In some embodiments, the induction step may be used any of the methods described herein. In some embodiment, the induction step is followed by the administration of the dosage regimens for R(+) pramipexole described herein as well as any of the compositions described herein.

Each of the pharmaceutical compositions described herein, may be used in any of the methods or dosage regimens described herein.

In some embodiments, the pharmaceutical compositions for use in the methods described herein comprise R(+) pramipexole. In some embodiments, the pharmaceutical compositions for use in the methods described herein consist essentially of R(+) pramipexole. In some embodiments, the pharmaceutical compositions for use in the methods described herein consist of R(+) pramipexole. The composition may further comprise a pharmaceutically acceptable carrier.

The therapeutically effective amount of R(+) pramipexole in the compositions may preferably be about 25 mg to about 5,000 mg, about 50 mg to about 5,000 mg, from about 100 mg to about 3,000 mg, from about 150 mg to about 1,500 mg, from about 300 mg to about 1,500 mg, from about 500 mg to about 1,000 mg. In some embodiments, the therapeutically effective amount of R(+) pramipexole in the compositions may be about from about 25 mg to about 5,000 mg, from about 50 mg to about 5,000 mg, from about 100 mg to about 5,000 mg, from about 150 mg to about 5,000 mg from about 200 mg to about 5,000 mg, from about 250 mg to about 5,000 mg, from about 300 mg to about 5,000 mg, from about 400 mg to about 5,000 mg, from 450 mg to about 5,000 mg, from about 150 mg, to about 3,000 mg from about 200 mg, to about 3,000 mg, from about 250 mg to about 3,000 mg, from about 300 mg to about 3,000 mg, from about 400 mg to about 3,000 mg, from 450 mg to about 3,000 mg, from about 100 mg to about 1,000 mg, from about 150 mg to about 1,000 mg, from about 200 mg to about 1,000 mg, from about 250 mg to about 1,000 mg, from about 300 mg to about 1,000 mg, from about 400 mg to about 1,000 mg, from about 600 mg to about 1,000 mg, or from 450 mg to about 1,000 mg. In some embodiments, the therapeutically effective amount of R(+) pramipexole is from about 600 mg to about 900 mg. This dose may be administered as a single daily dose, or may be divided into several doses administered throughout the day, for example, 1 to 5 doses, preferably two or three doses per day. In some embodiments, the therapeutically effective amount of R(+) pramipexole is from about 50 mg to about 5,000 mg. In some embodiments, the therapeutically effective amount of R(+) pramipexole is from about 100 mg to about 3,000 mg. In some embodiments, the therapeutically effective amount of R(+) pramipexole is from about 150 mg to about 3,000 mg. In some embodiments, the therapeutically effective amount of R(+) pramipexole is from about 150 mg to about 5,000 mg. In some embodiments, the therapeutically effective amount of R(+) pramipexole is from about 300 mg to about 1500 mg. In some embodiments, the therapeutically effective amount of R(+) pramipexole is from about 500 mg to about 1,000 mg. In some embodiments, the therapeutically effective amount of R(+) pramipexole is from about 600 mg to about 1,000 mg. In some embodiments, the therapeutically effective amount of R(+) pramipexole is about 0.1 mg or more, about 1 mg or more, about 10 mg or more, about 100 mg or more, about 125 mg or more, about 150 mg or more, about 300 mg or more, about 400 mg or more, about 450 mg or more, about 500 mg or more, about 600 mg or more, about 700 mg or more, about 800 mg or more, about 1,000 mg or more, about 3,000 mg or more, or about 5,000 mg or more. In some embodiments, the therapeutically effective amount of R(+) pramipexole is greater than 0.1 mg, greater than 1 mg, greater than 10 mg, greater than 100 mg, greater than 125 mg, greater than 150 mg, greater than 300 mg, greater than 400 mg, greater than 450 mg, greater than 500 mg, greater than 600 mg, greater than 700 mg, greater than 800 mg, greater than 1,000 mg, greater than 3,000 mg or greater than 5,000 mg. In some embodiments, the composition is suitable for oral administration. In certain embodiments, such pharmaceutical compositions may be selected from solid dosage forms, liquid dosage forms and aerosol dosage forms. In some embodiments, the pharmaceutical composition suitable for oral administration is in solid dosage form. In some embodiments, the pharmaceutical composition suitable for oral administration is a capsule. In some embodiments, the pharmaceutical composition suitable for oral administration is a tablet. In some embodiments, the composition is a solid oral dosage form. In some embodiments, the pharmaceutical compositions comprising R(+) pramipexole are suitable for oral administration inhalation, intranasal, or intravenous administration.

The composition may have a chiral purity for R(+) pramipexole of at least 99.5%, preferably at least 99.6%, preferably at least 99.7%, preferably at least 99.8%, preferably at least 99.9%, preferably at least 99.95%, or more preferably at least 99.99%. In some embodiments, the chiral purity for R(+) pramipexole is 100%. In some embodiments, the composition has a chiral purity for R(+) pramipexole of 99.9% or greater. In some embodiments, the composition has a chiral purity for R(+) pramipexole of 99.95% or greater. In some embodiments, the composition has a chiral purity for R(+) pramipexole of 99.99% or greater. The high chiral purity of the pramipexole used herein, R(+) pramipexole, allows for therapeutic compositions that may have a wide individual and daily dose range.

The embodiments for amounts of R(+) pramipexole in the composition, chiral purity, and dosage form, which are described herein separately for the sake of brevity, can be joined in any suitable combination.

In a further aspect, the present invention further provides a composition comprising a therapeutically effective amount of R(+) pramipexole and a non-effective dose amount of (S)-pramipexole.

In some embodiments, the non-effective dose amount of (S)-pramipexole is an amount that does not exceed about 1.0 mg. In more preferred embodiments, the non-effective dose amount of (S)-pramipexole is an amount that does not exceed about 0.75 mg, about 0.5 mg, about 0.25 mg, about 0.125 mg or about 0.05 mg. In some embodiments, the non-effective dose amount of (S)-pramipexole is less than about 0.125 mg. In some embodiments, the non-effective dose amount of (S)-pramipexole is less than about 0.05 mg. In some embodiments, the therapeutically effective amount of R(+) pramipexole and a non-effective dose amount of (S)-pramipexole are administered in a single unit dose form In another aspect, the present invention provides a composition comprising a therapeutically effective amount of R(+) pramipexole and a no observable adverse effect level (NOAEL) dose amount of (S)-pramipexole. A NOAEL dose as used herein refers to an amount of active compound or pharmaceutical agent that produces no statistically or biologically significant increases in the frequency or severity of adverse effects between an exposed population and its appropriate control; some effects may be produced at this level, but they are not considered as adverse, or as precursors to adverse effects. The exposed population may be a system, tissue, animal, individual or human that is being treated by a researcher, veterinarian, medical doctor or other clinician.

The therapeutic composition may further comprise a pharmaceutically acceptable carrier.

In some embodiments, the no observable adverse effect level dose amount of (S)-pramipexole is less than about 1.50 mg. In some embodiments, the no observable adverse effect level amount of (S)-pramipexole is less than about 0.5 mg. In some embodiments, the no observable adverse effect level amount of (S)-pramipexole is less than about 0.05 mg. In some embodiments, the therapeutically effective amount of R(+) pramipexole and the NOAEL dose amount of (S)-pramipexole are administered in a single unit dose form In some embodiments, the composition comprises about 150 mg of R(+) pramipexole and no more than about 1.0 mg of (S)-pramipexole. In some embodiments, the composition comprises about 150 mg of R(+) pramipexole and no more than about 0.333 mg of (S)-pramipexole. In some embodiments, the composition comprises about 150 mg of R(+) pramipexole and no more than about 0.3 mg of (S)-pramipexole. In some embodiments, the composition comprises about 150 mg of R(+) pramipexole and no more than about 0.2 mg of (S)-pramipexole. In some embodiments, the composition comprises about 150 mg of R(+) pramipexole and no more than about 0.125 mg of (S)-pramipexole.

In some embodiments, the composition comprises about 200 mg of R(+) pramipexole and no more than about 1.0 mg of (S)-pramipexole. In some embodiments, the composition comprises about 200 mg of R(+) pramipexole and no more than about 0.333 mg of (S)-pramipexole. In some embodiments, the composition comprises about 200 mg of R(+) pramipexole and no more than about 0.3 mg of (S)-pramipexole. In some embodiments, the composition comprises about 200 mg of R(+) pramipexole and no more than about 0.2 mg of (S)-pramipexole. In some embodiments, the composition comprises about 200 mg of R(+) pramipexole and no more than about 0.125 mg of (S)-pramipexole.

In some embodiments, the composition comprises about 250 mg of R(+) pramipexole and no more than about 1.0 mg of (S)-pramipexole. In some embodiments, the composition comprises about 250 mg of R(+) pramipexole and no more than about 0.333 mg of (S)-pramipexole. In some embodiments, the composition comprises about 250 mg of R(+) pramipexole and no more than about 0.3 mg of (S)-pramipexole. In some embodiments, the composition comprises about 250 mg of R(+) pramipexole and no more than about 0.2 mg of (S)-pramipexole. In some embodiments, the composition comprises about 250 mg of R(+) pramipexole and no more than about 0.125 mg of (S)-pramipexole.

In some embodiments, the composition comprises about 500 mg of R(+) pramipexole and no more than about 1.0 mg of (S)-pramipexole. In some embodiments, the composition comprises about 500 mg of R(+) pramipexole and no more than about 0.333 mg of (S)-pramipexole. In some embodiments, the composition comprises about 500 mg of R(+) pramipexole and no more than about 0.3 mg of (S)-pramipexole. In some embodiments, the composition comprises about 500 mg of R(+) pramipexole and no more than about 0.2 mg of (S)-pramipexole. In some embodiments, the composition comprises about 500 mg of R(+) pramipexole and no more than about 0.125 mg of (S)-pramipexole.

In some embodiments, the composition comprises about 600 mg of R(+) pramipexole and no more than about 1.0 mg of (S)-pramipexole. In some embodiments, the composition comprises about 600 mg of R(+) pramipexole and no more than about 0.333 mg of (S)-pramipexole. In some embodiments, the composition comprises about 600 mg of R(+) pramipexole and no more than about 0.3 mg of (S)-pramipexole. In some embodiments, the composition comprises about 600 mg of R(+) pramipexole and no more than about 0.2 mg of (S)-pramipexole. In some embodiments, the composition comprises about 600 mg of R(+) pramipexole and no more than about 0.125 mg of (S)-pramipexole.

In some embodiments, the composition comprises about 1,000 mg of R(+) pramipexole and no more than about 1.0 mg of (S)-pramipexole. In some embodiments, the composition comprises about 1,000 mg of R(+) pramipexole and no more than about 0.333 mg of (S)-pramipexole. In some embodiments, the composition comprises about 1,000 mg of R(+) pramipexole and no more than about 0.3 mg of (S)-pramipexole. In some embodiments, the composition comprises about 1,000 mg of R(+) pramipexole and no more than about 0.2 mg of (S)-pramipexole. In some embodiments, the composition comprises about 1,000 mg of R(+) pramipexole and no more than about 0.125 mg of (S)-pramipexole.

In another aspect, the present invention provides a starting daily dose of R(+) pramipexole of about 25 mg or more of R(+) pramipexole. In some embodiments, the starting daily dose comprises about 50 mg or more of R(+) pramipexole. In some embodiments, the starting daily dose comprises about 75 mg or more of R(+) pramipexole. In some embodiments, the starting daily dose comprises about 125 mg or more of R(+) pramipexole. In some embodiments, the starting daily dose comprises about 150 mg or more of R(+) pramipexole. In some embodiments, the starting daily dose comprises about 200 mg or more of R(+) pramipexole. In some embodiments, the starting daily dose comprises about 300 mg or more of R(+) pramipexole. In some embodiments, the starting daily dose comprises about 400 mg or more of R(+) pramipexole. In some embodiments, the starting daily dose comprises about 500 mg or more of R(+) pramipexole. In some embodiments, the starting daily dose comprises about 600 mg or more of R(+) pramipexole. In some embodiments, the starting daily dose comprises about 750 mg or more of R(+) pramipexole. In some embodiments, the starting daily dose comprises about least about 1,000 mg or more of R(+) pramipexole. In certain embodiments, the starting daily dose comprises about 0.1 mg or more, about 1 mg or more, about 10 mg or more, about 100 mg or more, about 125 mg or more, about 150 mg or more, about 300 mg or more, about 400 mg or more, about 450 mg or more, about 500 mg or more, about 600 mg or more, about 700 mg or more, about 800 mg or more, about 1,000 mg or more, about 3,000 mg or more, or about 5,000 mg or more, of R(+) pramipexole and in still other embodiments the starting daily dose comprises greater than 0.1 mg, greater than 1 mg, greater than 10 mg, greater than 100 mg, greater than 125 mg, greater than 150 mg, greater than 300 mg, greater than 400 mg, greater than 450 mg, greater than 500 mg, greater than 600 mg, greater than 700 mg, greater than 800 mg, or greater than 1,000 mg, greater than 1,200 mg, or greater than 1,500 mg of R(+) pramipexole. In some embodiments, the starting daily dose comprises from about 600 mg to about 900 mg of R(+) pramipexole.

In some embodiments, the starting daily dose amount may be 10 mg/day to 1,500 mg/day, more preferably 100 mg/day to 600 mg/day. In yet other embodiments, the starting daily dose amount may be 150 mg/day to 5,000 mg/day. The starting daily dose amount of R(+) pramipexole in the compositions may preferably be about 50 mg to about 5,000 mg, from about 100 mg to about 3,000 mg, from about 150 mg to about 3,000 mg, from about 300 mg to about 1,500 mg, from about 500 mg to about 1,000 mg. In some embodiments, the starting daily dose amount of R(+) pramipexole in the compositions may be about from about 25 mg to about 5,000 mg, from about 50 mg to about 5,000 mg, from about 100 mg to about 5,000 mg, from about 150 mg to about 5,000 mg, from about 200 mg to about 5,000 mg, from about 250 mg to about 5,000 mg, from about 300 mg to about 5,000 mg, from about 400 mg to about 5,000 mg, from 450 mg to about 5,000 mg, from about 150 mg to about 5,000 mg from about 200 mg to about 3,000 mg, from about 150 mg to about 3,000 mg, from about 300 mg to about 3,000 mg, from about 400 mg to about 3,000 mg, from 450 mg to about 3,000 mg, from about 100 mg to about 1,000 mg, from about 150 mg to about 1,000 mg, from about 200 mg to about 1,000 mg, from about 250 mg to about 1,000 mg, from about 300 mg to about 1,000 mg, from about 400 mg to about 1,000 mg, from about 600 mg to about 1,000 mg, or from 450 mg to about 1,000 mg. In some embodiments, the starting daily dose amount of R(+) pramipexole is from about 600 mg to about 900 mg. This dose may be administered as a single daily dose, or may be divided into several doses administered throughout the day, for example, 1 to 5 doses per day, preferably two to three doses per day. In some embodiments, the starting daily dose amount of R(+) pramipexole is from about 150 mg to about 5,000 mg. In some embodiments, the starting daily dose amount of R(+) pramipexole is from about 150 mg to about 3,000 mg. In some embodiments, the starting daily dose amount of R(+) pramipexole is from about 300 mg to about 1500 mg. In some embodiments, the starting daily dose amount of R(+) pramipexole is from about 500 mg to about 1,000 mg.

In another aspect, the present invention provides a starting daily dose comprising at least about 100 mg of R(+) pramipexole and no more than about 1.5 mg of (S)-pramipexole. In some embodiments, the starting daily dose comprises about 150 mg of R(+) pramipexole. In some embodiments, the starting daily dose comprises about 200 mg of R(+) pramipexole. In some embodiments, the starting daily dose comprises about 250 mg of R(+) pramipexole. In some embodiments, the starting daily dose comprises about 500 mg of R(+) pramipexole. In some embodiments, the starting daily dose comprises about 1,000 mg of R(+) pramipexole. In certain embodiments, the starting daily dose comprises about 0.1 mg or more, about 1 mg or more, about 10 mg or more, about 100 mg or more, about 125 mg or more, about 150 mg or more, about 300 mg or more, about 400 mg or more, about 450 mg or more, about 500 mg or more, about 600 mg or more, about 700 mg or more, about 800 mg or more, about 1,000 mg or more, about 3,000 mg or more, or about 5,000 mg or more, of R(+) pramipexole and in still other embodiments the starting daily dose comprises greater than 0.1 mg, greater than 1 mg, greater than 10 mg, greater than 100 mg, greater than 125 mg, greater than 150 mg, greater than 300 mg, greater than 400 mg, greater than 450 mg, greater than 500 mg, greater than 600 mg, greater than 700 mg, greater than 800 mg, or greater than 1,000 mg of R(+) pramipexole. In some embodiments, the starting daily dose comprises no more than 1.0 mg of (S)-pramipexole. In some embodiments, the starting daily dose comprises no more than 0.333 mg of (S)-pramipexole. In some embodiments, the starting daily dose comprises no more than 0.3 mg of (S)-pramipexole. In some embodiments, the starting daily dose comprises no more than 0.2 mg of (S)-pramipexole. In some embodiments, the starting daily dose comprises no more than 0.125 mg of (S)-pramipexole. In some embodiments, the starting daily dose further comprises a pharmaceutically acceptable carrier. In some embodiments, the composition is suitable for oral administration. In some embodiments, the composition is a solid oral dosage form. In some embodiments, the pharmaceutical composition is a tablet. In some embodiments, the pharmaceutical composition is a capsule.

In some embodiments, the starting daily dose comprises about 150 mg of R(+) pramipexole and no more than about 1.0 mg of (S)-pramipexole. In some embodiments, the starting daily dose comprises about 150 mg of R(+) pramipexole and no more than about 0.333 mg of (S)-pramipexole. In some embodiments, the starting daily dose comprises about 150 mg of R(+) pramipexole and no more than about 0.3 mg of (S)-pramipexole. In some embodiments, the starting daily dose comprises about 150 mg of R(+) pramipexole and no more than about 0.2 mg of (S)-pramipexole. In some embodiments, the starting daily dose comprises about 150 mg of R(+) pramipexole and no more than about 0.125 mg of (S)-pramipexole.

In some embodiments, the starting daily dose comprises about 200 mg of R(+) pramipexole and no more than about 1.0 mg of (S)-pramipexole. In some embodiments, the starting daily dose comprises about 200 mg of R(+) pramipexole and no more than about 0.333 mg of (S)-pramipexole. In some embodiments, the starting daily dose comprises about 200 mg of R(+) pramipexole and no more than about 0.3 mg of (S)-pramipexole. In some embodiments, the starting daily dose comprises about 200 mg of R(+) pramipexole and no more than about 0.2 mg of (S)-pramipexole. In some embodiments, the starting daily dose comprises about 200 mg of R(+) pramipexole and no more than about 0.125 mg of (S)-pramipexole.

In some embodiments, the starting daily dose comprises about 250 mg of R(+) pramipexole and no more than about 1.0 mg of (S)-pramipexole. In some embodiments, the starting daily dose comprises about 250 mg of R(+) pramipexole and no more than about 0.333 mg of (S)-pramipexole. In some embodiments, the starting daily dose comprises about 250 mg of R(+) pramipexole and no more than about 0.3 mg of (S)-pramipexole. In some embodiments, the starting daily dose comprises about 250 mg of R(+) pramipexole and no more than about 0.2 mg of (S)-pramipexole. In some embodiments, the starting daily dose comprises about 250 mg of R(+) pramipexole and no more than about 0.125 mg of (S)-pramipexole.

In some embodiments, the starting daily dose comprises about 500 mg of R(+) pramipexole and no more than about 1.0 mg of (S)-pramipexole. In some embodiments, the starting daily dose comprises about 500 mg of R(+) pramipexole and no more than about 0.333 mg of (S)-pramipexole. In some embodiments, the starting daily dose comprises about 500 mg of R(+) pramipexole and no more than about 0.3 mg of (S)-pramipexole. In some embodiments, the starting daily dose comprises about 500 mg of R(+) pramipexole and no more than about 0.2 mg of (S)-pramipexole. In some embodiments, the starting daily dose comprises about 500 mg of R(+) pramipexole and no more than about 0.125 mg of (S)-pramipexole.

In some embodiments, the starting daily dose comprises about 600 mg of R(+) pramipexole and no more than about 1.0 mg of (S)-pramipexole. In some embodiments, the starting daily dose comprises about 600 mg of R(+) pramipexole and no more than about 0.333 mg of (S)-pramipexole. In some embodiments, the starting daily dose comprises about 600 mg of R(+) pramipexole and no more than about 0.3 mg of (S)-pramipexole. In some embodiments, the starting daily dose comprises about 600 mg of R(+) pramipexole and no more than about 0.2 mg of (S)-pramipexole. In some embodiments, the starting daily dose comprises about 600 mg of R(+) pramipexole and no more than about 0.125 mg of (S)-pramipexole.

In some embodiments, the starting daily dose comprises about 1,000 mg of R(+) pramipexole and no more than about 1.0 mg of (S)-pramipexole. In some embodiments, the starting daily dose comprises about 1,000 mg of R(+) pramipexole and no more than about 0.333 mg of (S)-pramipexole. In some embodiments, the starting daily dose comprises about 1,000 mg of R(+) pramipexole and no more than about 0.3 mg of (S)-pramipexole. In some embodiments, the starting daily dose comprises about 1,000 mg of R(+) pramipexole and no more than about 0.2 mg of (S)-pramipexole. In some embodiments, the starting daily dose comprises about 1,000 mg of R(+) pramipexole and no more than about 0.125 mg of (S)-pramipexole.

In another aspect, the present invention provides a single unit dose of R(+) pramipexole of about 25 mg or more of R(+) pramipexole. In some embodiments, the single unit dose comprises about 50 mg or more of R(+) pramipexole. In some embodiments, the single unit dose comprises about 75 mg or more of R(+) pramipexole. In some embodiments, the single unit dose comprises about 125 mg or more of R(+) pramipexole. In some embodiments, the single unit dose comprises about 150 mg or more of R(+) pramipexole. In some embodiments, the single unit dose comprises about 200 mg or more of R(+) pramipexole. In some embodiments, the single unit dose comprises about 300 mg or more of R(+) pramipexole. In some embodiments, the single unit dose comprises about 400 mg or more of R(+) pramipexole. In some embodiments, the single unit dose comprises about 500 mg or more of R(+) pramipexole. In some embodiments, the single unit dose comprises about 600 mg or more of R(+) pramipexole. In some embodiments, the single unit dose comprises about 750 mg or more of R(+) pramipexole. In some embodiments, the single unit dose comprises about 1,000 mg or more of R(+) pramipexole. In certain embodiments, the single unit dose comprises about 0.1 mg or more, about 1 mg or more, about 10 mg or more, about 100 mg or more, about 125 mg or more, about 150 mg or more, about 300 mg or more, about 400 mg or more, about 450 mg or more, about 500 mg or more, about 600 mg or more, about 700 mg or more, about 800 mg or more, about 1,000 mg or more, about 3,000 mg or more, or about 5,000 mg or more, of R(+) pramipexole and in still other embodiments the single unit dose comprises greater than 0.1 mg, greater than 1 mg, greater than 10 mg, greater than 100 mg, greater than 125 mg, greater than 150 mg, greater than 300 mg, greater than 400 mg, greater than 450 mg, greater than 500 mg, greater than 600 mg, greater than 700 mg, greater than 800 mg, or greater than 1,000 mg, greater than 1,200 mg, or greater than 1,500 mg of R(+) pramipexole. In some embodiments, the single unit dose comprises from about 600 mg to about 900 mg of R(+) pramipexole.

In some embodiments, the single unit dose amount may be 10 mg/day to 1,500 mg/day, more preferably 100 mg/day to 600 mg/day. In yet other embodiments, the single unit dose amount may be 150 mg/day to 5,000 mg/day. The single unit dose amount of R(+) pramipexole in the compositions may preferably be about 50 mg to about 5,000 mg, from about 100 mg to about 3,000 mg, from about 150 mg to about 3,000 mg, from about 300 mg to about 1,500 mg, from about 500 mg to about 1,000 mg. In some embodiments, the single unit dose amount of R(+) pramipexole in the compositions may be about from about 25 mg to about 5,000 mg, from about 50 mg to about 5,000 mg, from about 100 mg to about 5,000 mg, from about 150 mg to about 5,000 mg, from about 200 mg to about 5,000 mg, from about 250 mg to about 5,000 mg, from about 300 mg to about 5,000 mg, from about 400 mg to about 5,000 mg, from 450 mg to about 5,000 mg, from about 150 mg to about 5,000 mg from about 200 mg to about 3,000 mg, from about 150 mg to about 3,000 mg, from about 300 mg to about 3,000 mg, from about 400 mg to about 3,000 mg, from 450 mg to about 3,000 mg, from about 100 mg to about 1,000 mg, from about 150 mg to about 1,000 mg, from about 200 mg to about 1,000 mg, from about 250 mg to about 1,000 mg, from about 300 mg to about 1,000 mg, from about 400 mg to about 1,000 mg, from about 600 mg to about 1,000 mg, or from 450 mg to about 1,000 mg. In some embodiments, the single unit dose amount of R(+) pramipexole is from about 600 mg to about 900 mg. In some embodiments, the single unit dose amount of R(+) pramipexole is from about 150 mg to about 5,000 mg. In some embodiments, the single unit dose amount of R(+) pramipexole is from about 150 mg to about 3,000 mg. In some embodiments, the single unit dose of R(+) pramipexole is from about 300 mg to about 1500 mg. In some embodiments, the single unit dose amount of R(+) pramipexole is from about 500 mg to about 1,000 mg.

In another aspect, the present invention provides a single unit dose comprising at least about 100 mg of R(+) pramipexole and no more than about 1.5 mg of (S)-pramipexole. In some embodiments, the single unit dose comprises about 150 mg of R(+) pramipexole. In some embodiments, the single unit dose comprises about 200 mg of R(+) pramipexole. In some embodiments, the single unit dose comprises about 250 mg of R(+) pramipexole. In some embodiments, the single unit dose comprises about 500 mg of R(+) pramipexole. In some embodiments, the single unit dose comprises about 1,000 mg of R(+) pramipexole. In certain embodiments, the single unit dose comprises about 0.1 mg or more, about 1 mg or more, about 10 mg or more, about 100 mg or more, about 125 mg or more, about 150 mg or more, about 300 mg or more, about 400 mg or more, about 450 mg or more, about 500 mg or more, about 600 mg or more, about 700 mg or more, about 800 mg or more, about 1,000 mg or more, about 3,000 mg or more, or about 5,000 mg or more, of R(+) pramipexole and in still other embodiments the single unit dose comprises greater than 0.1 mg, greater than 1 mg, greater than 10 mg, greater than 100 mg, greater than 125 mg, greater than 150 mg, greater than 300 mg, greater than 400 mg, greater than 450 mg, greater than 500 mg, greater than 600 mg, greater than 700 mg, greater than 800 mg, or greater than 1,000 mg of R(+) pramipexole. In some embodiments, the single unit dose comprises no more than 1.0 mg of (S)-pramipexole. In some embodiments, the single unit dose comprises no more than 0.333 mg of (S)-pramipexole. In some embodiments, the single unit dose comprises no more than 0.3 mg of (S)-pramipexole. In some embodiments, the single unit dose comprises no more than 0.2 mg of (S)-pramipexole. In some embodiments, the single unit dose comprises no more than 0.125 mg of (S)-pramipexole. In some embodiments, the single unit dose further comprises a pharmaceutically acceptable carrier. In some embodiments, the composition is suitable for oral administration. In some embodiments, the composition is a solid oral dosage form. In some embodiments, the pharmaceutical composition is a tablet. In some embodiments, the pharmaceutical composition is a capsule. In some embodiments, such single unit doses may be administered once per day or multiple times per day, such as twice per day or three times per day.

In some embodiments, the single unit dose comprises about 150 mg of R(+) pramipexole and no more than about 1.0 mg of (S)-pramipexole. In some embodiments, the single unit dose comprises about 150 mg of R(+) pramipexole and no more than about 0.333 mg of (S)-pramipexole. In some embodiments, the single unit dose comprises about 150 mg of R(+) pramipexole and no more than about 0.3 mg of (S)-pramipexole. In some embodiments, the single unit dose comprises about 150 mg of R(+) pramipexole and no more than about 0.2 mg of (S)-pramipexole. In some embodiments, the single unit dose comprises about 150 mg of R(+) pramipexole and no more than about 0.125 mg of (S)-pramipexole.

In some embodiments, the single unit dose comprises about 200 mg of R(+) pramipexole and no more than about 1.0 mg of (S)-pramipexole. In some embodiments, the single unit dose comprises about 200 mg of R(+) pramipexole and no more than about 0.333 mg of (S)-pramipexole. In some embodiments, the single unit dose comprises about 200 mg of R(+) pramipexole and no more than about 0.3 mg of (S)-pramipexole. In some embodiments, the single unit dose comprises about 200 mg of R(+) pramipexole and no more than about 0.2 mg of (S)-pramipexole. In some embodiments, the single unit dose comprises about 200 mg of R(+) pramipexole and no more than about 0.125 mg of (S)-pramipexole.

In some embodiments, the single unit dose comprises about 250 mg of R(+) pramipexole and no more than about 1.0 mg of (S)-pramipexole. In some embodiments, the single unit dose comprises about 250 mg of R(+) pramipexole and no more than about 0.333 mg of (S)-pramipexole. In some embodiments, the single unit dose comprises about 250 mg of R(+) pramipexole and no more than about 0.3 mg of (S)-pramipexole. In some embodiments, the single unit dose comprises about 250 mg of R(+) pramipexole and no more than about 0.2 mg of (S)-pramipexole. In some embodiments, the single unit dose comprises about 250 mg of R(+) pramipexole and no more than about 0.125 mg of (S)-pramipexole.

In some embodiments, the single unit dose comprises about 500 mg of R(+) pramipexole and no more than about 1.0 mg of (S)-pramipexole. In some embodiments, the single unit dose comprises about 500 mg of R(+) pramipexole and no more than about 0.333 mg of (S)-pramipexole. In some embodiments, the single unit dose comprises about 500 mg of R(+) pramipexole and no more than about 0.3 mg of (S)-pramipexole. In some embodiments, the single unit dose comprises about 500 mg of R(+) pramipexole and no more than about 0.2 mg of (S)-pramipexole. In some embodiments, the single unit dose comprises about 500 mg of R(+) pramipexole and no more than about 0.125 mg of (S)-pramipexole.

In some embodiments, the single unit dose comprises about 600 mg of R(+) pramipexole and no more than about 1.0 mg of (S)-pramipexole. In some embodiments, the single unit dose comprises about 600 mg of R(+) pramipexole and no more than about 0.333 mg of (S)-pramipexole. In some embodiments, the single unit dose comprises about 600 mg of R(+) pramipexole and no more than about 0.3 mg of (S)-pramipexole. In some embodiments, the single unit dose comprises about 600 mg of R(+) pramipexole and no more than about 0.2 mg of (S)-pramipexole. In some embodiments, the single unit dose comprises about 600 mg of R(+) pramipexole and no more than about 0.125 mg of (S)-pramipexole.

In some embodiments, the single unit dose comprises about 1,000 mg of R(+) pramipexole and no more than about 1.0 mg of (S)-pramipexole. In some embodiments, the single unit dose comprises about 1,000 mg of R(+) pramipexole and no more than about 0.333 mg of (S)-pramipexole. In some embodiments, the single unit dose comprises about 1,000 mg of R(+) pramipexole and no more than about 0.3 mg of (S)-pramipexole. In some embodiments, the single unit dose comprises about 1,000 mg of R(+) pramipexole and no more than about 0.2 mg of (S)-pramipexole. In some embodiments, the single unit dose comprises about 1,000 mg of R(+) pramipexole and no more than about 0.125 mg of (S)-pramipexole.

In another aspect, the present invention provides a pharmaceutical formulation comprising microcrystalline cellulose in an amount from about 20% to about 50% by weight of said formulation; mannitol in about from about 10% to about 30% by weight of said formulation; crospovidone in an amount from about 2% to about 6% of said formulation; magnesium stearate in an amount from about 0.01% to about 2% of said composition; and R(+) pramipexole. In some embodiments, the pharmaceutical composition comprises a diluent in an amount from about 20% to about 50% by weight of said formulation; optionally, a second diluent in an amount from about 10% to about 30% by weight of said formulation; optionally, a disintegrant in an amount from about 2% to about 6% of said formulation; optionally, a lubricant in an amount from about 0.01% to about 2% of said composition; and R(+) pramipexole. In some embodiments, the pharmaceutical composition microcrystalline cellulose, mannitol, croscarmellose sodium, magnesium stearate, or combination thereof. In some embodiments, the pharmaceutically acceptable carrier comprises microcrystalline cellulose, mannitol or combination thereof; and further optionally comprises croscarmellose sodium or magnesium stearate, or combination thereof.

The amount of R(+) pramipexole in the formulation may preferably be about 50 mg to about 5,000 mg, from about 100 mg to about 3,000 mg, from about 150 mg to about 3,000 mg, from about 300 mg to about 1,500 mg, from about 500 mg to about 1,000 mg. In some embodiments, the starting daily dose amount of R(+) pramipexole in the formulation may be about from about 25 mg to about 5,000 mg, from about 50 mg to about 5,000 mg, from about 100 mg to about 5,000 mg, from about 150 mg to about 5,000 mg, from about 200 mg to about 5,000 mg, from about 250 mg to about 5,000 mg, from about 300 mg to about 5,000 mg, from about 400 mg to about 5,000 mg, from 450 mg to about 5,000 mg, from about 150 mg to about 3,000 mg, from about 200 mg, to about 3,000 mg, from about 250 mg to about 3,000 mg, from about 300 mg to about 3,000 mg, from about 400 mg to about 3,000 mg, from 450 mg to about 3,000 mg, from about 100 mg to about 1,000 mg, from about 150 mg to about 3,000 mg, from about 200 mg to about 1,000 mg, from about 250 mg to about 1,000 mg, from about 300 mg to about 1,000 mg, from about 400 mg to about 1,000 mg, from about 600 mg to about 1,000 mg, or from 450 mg to about 1,000 mg. In some embodiments, the formulation of R(+) pramipexole is from about 600 mg to about 900 mg. In certain embodiments, the formulation of R(+) pramipexole comprises about 0.1 mg or more, about 1 mg or more, about 10 mg or more, about 100 mg or more, about 125 mg or more, about 150 mg or more, about 300 mg or more, about 400 mg or more, about 450 mg or more, about 500 mg or more, about 600 mg or more, about 700 mg or more, about 800 mg or more, about 1,000 mg or more, about 3,000 mg or more, or about 5,000 mg or more, of R(+) pramipexole and in still other embodiments the formulation of R(+) pramipexole comprises greater than 0.1 mg, greater than 1 mg, greater than 10 mg, greater than 100 mg, greater than 125 mg, greater than 150 mg, greater than 300 mg, greater than 400 mg, greater than 450 mg, greater than 500 mg, greater than 600 mg, greater than 700 mg, greater than 800 mg, or greater than 1,000 mg, greater than 1,200 mg, or greater than 1,500 mg of R(+) pramipexole.

In some embodiments, the pharmaceutical compositions described herein may further comprise microcrystalline cellulose in an amount from about 20% to about 50% by weight of said composition; mannitol in an amount from about 10% to about 30% by weight of said composition; crospovidone in an amount from about 2% to about 6% of said composition; magnesium stearate in an amount from about 0.01% to about 2% of said composition; and R(+) pramipexole. I In some embodiments, the compositions described herein may be formulated as a pharmaceutical or therapeutic composition by combining with one or more pharmaceutically acceptable carriers. Embodiments include pharmaceutical or therapeutic compositions that may be administered orally, by inhalation, intranasally, or via intravenous administration. Embodiments include pharmaceutical or therapeutic compositions that may be administered orally preferably as a solid oral dose, and more preferably as a solid oral dose that may be a capsule or tablet. In a preferred embodiment, the pharmaceutical or therapeutic composition is formulated in tablet or capsule form for use in oral administration routes. The compositions and amounts of non-active ingredients in such a formulation may depend on the amount of the active ingredient, and on the size and shape of the tablet or capsule. Such parameters may be readily appreciated and understood by one of skill in the art.

The pharmaceutical or therapeutic compositions described herein may be prepared, packaged, sold in bulk, as a single unit dose, or as multiple unit doses and can be administered in the conventional manner by any route where they are active. For example, the compositions may be administered orally, ophthalmically, intravenously, intramuscularly, intra-arterially, intramedullary, intrathecally, intraventricularly, transdermally, subcutaneously, intraperitoneally, intravesicularly, intranasally, enterally, topically, sublingually, rectally, by inhalation, by depot injections, or by implants or by use of vaginal creams, suppositories, pessaries, vaginal rings, rectal suppositories, intrauterine devices, and transdermal forms such as patches and creams. Specific modes of administration will depend on the indication. The selection of the specific route of administration and the dose regimen may be adjusted or titrated by the clinician according to known methods in order to obtain the optimal clinical response. All of the methods described herein may be carried out by administering R(+) pramipexole by any such route for administration described herein. Additionally, R(+) pramipexole may be delivered by using any such route of administration for all of the dosage regimens described herein.

The doses of the R(+) pramipexole may be administered to a patient in need thereof. This dose may be administered as a single daily dose, or may be divided into several doses, which are administered throughout the day, such as 1 to 5 doses, or two to three doses per day. The route of administration may include oral, sublingual, transdermal, rectal, or any accessible parenteral route. One of ordinary skill in the art will understand and appreciate the dosages and timing of the dosages to be administered to a patient in need thereof. The doses and duration of treatment may vary, and may be based on assessment by one of ordinary skill in the art based on monitoring and measuring improvements in neuronal and non-neuronal tissues. This assessment may be made based on outward physical signs of improvement, such as increased muscle control, or on internal physiological signs or markers. The doses may also depend on the condition or disease being treated, the degree of the condition or disease being treated and further on the age and weight of the patient.

Specific modes of administration will depend on the indication. The selection of the specific route of administration and the dose regimen may be adjusted or titrated by the clinician according to methods known to the clinician in order to obtain the optimal clinical response. The amount of compound to be administered may be that amount which is therapeutically effective. The dosage to be administered may depend on the characteristics of the subject being treated, e.g., the particular animal or human subject treated, age, weight, health, types of concurrent treatment, if any, and frequency of treatments, and can be easily determined by one of skill in the art (e.g., by the clinician).

Pharmaceutical formulations containing R(+) pramipexole in a solid dosage may include, but are not limited to, tablets, capsules, cachets, pellets, pills, powders and granules; topical dosage forms which include, but are not limited to, solutions, powders, fluid emulsions, fluid suspensions, semi-solids, ointments, pastes, creams, gels and jellies, and foams; and parenteral dosage forms which include, but are not limited to, solutions, suspensions, emulsions, and dry powder; comprising an effective amount of a polymer or copolymer of the present invention. It is also known in the art that the active ingredients can be contained in such formulations with pharmaceutically acceptable diluents, fillers, disintegrants, binders, lubricants, surfactants, hydrophobic vehicles, water-soluble vehicles, emulsifiers, buffers, humectants, moisturizers, solubilizers, preservatives and the like. The means and methods for administration are known in the art and an artisan can refer to various pharmacologic references for guidance. For example, Modern Pharmaceutics, Banker & Rhodes, Marcel Dekker, Inc. (1979); and Goodman & Gilman's The Pharmaceutical Basis of Therapeutics, 6th Edition, MacMillan Publishing Co., New York (1980) can be consulted.

For oral administration, the compounds can be formulated readily by combining these compounds with pharmaceutically acceptable carriers well known in the art. Such carriers enable the compounds to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethylcellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

In some embodiments, pharmaceutical compositions may be suitable for oral administration such as, for example, a solid oral dosage form or a capsule, and in certain embodiments, the composition may be a tablet. Such tablets may include any number of additional agents such as, for example, one or more binder, one or more lubricant, one or more diluent, one or more lubricant, one or more surface active agent, one or more dispersing agent, one or more colorant, and the like. Such tablets may be prepared by any method known in the art, for example, by compression or molding. Compressed tablets may be prepared by compressing in a suitable machine the ingredients of the composition in a free-flowing form such as a powder or granules, and molded tablets may be made by molding in a suitable machine a mixture of the powdered compound moistened with an inert liquid diluent. The tablets, of some embodiments, may be uncoated and, in other embodiments, they may be coated by known techniques.

In other embodiments prepared for oral administration, the pharmaceutical compositions may be provided in a dragee core with suitable coatings. In such embodiments, dragee cores may be prepared using concentrated sugar solutions, which may optionally contain gum arabic, talc, polyvinyl pyrrolidone, carbopol gel, polyethylene glycol, and/or titanium dioxide, lacquer solutions, and suitable organic solvents or solvent mixtures. In some embodiments, dyestuffs or pigments may be added to the tablets or dragee coatings for identification or to characterize different combinations of active compound doses. In yet other embodiments, pharmaceutical compositions including a therapeutically effective amount of R(+) pramipexole prepared for oral administration may include, but are not limited to, push-fit capsules made of gelatin, as well as soft, sealed capsules made of gelatin and a plasticizer, such as glycerol or sorbitol. The push-fit capsules can contain the active ingredients in admixture with filler such as, e.g., lactose, binders such as, e.g., starches, and/or lubricants such as, e.g., talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

In embodiments in which the tablets and dragee cores are coated, the coatings may delay disintegration and absorption in the gastrointestinal tract and thereby providing a sustained action over a longer period. Additionally, such coatings may be adapted for release of R(+) pramipexole in a predetermined pattern (e.g., in order to achieve a controlled release formulation) or it may be adapted not to release the active compound until after passage of the stomach (enteric coating). Suitable coatings encompassed by such embodiments may include, but are not limited to, sugar coating, film coating (e.g., hydroxypropyl methylcellulose, methylcellulose, methyl hydroxyethy 1 cellulose, hydroxypropy 1 cellulose, carboxymethylcellulose, acrylate copolymers, polyethylene glycols and/or polyvinylpyrrolidone), or an enteric coating (e.g., methacrylic acid copolymer, cellulose acetate phthalate, hydroxypropylmethylcellulose phthalate, hydroxypropyl methylcellulose acetate succinate, polyvinyl acetate phthalate, shellac, and/or ethyl cellulose). Furthermore, a time delay material such as, for example, glyceryl monostearate or glyceryl distearate may be incorporated into the coatings of some embodiments. In still other embodiments, solid tablet compositions may include a coating adapted to protect the composition from unwanted chemical changes, for example, to reduce chemical degradation prior to the release of the active drug sub stance.

Pharmaceutical composition suitable for oral administration encompassed in these embodiments may include a therapeutically effective amount of R(+) pramipexole and a non-effective dose amount of another therapeutic agent and may further include one or more diluent, one or more disintegrant, one or more lubricant, one or more pigment or colorant, one or more gelatin, one or more plasticizer and the like. For example, in some embodiments, a tablet may include R(+) pramipexole, from about 20% to about 50% by weight of diluent in an amount, from about 100% to about 30% by weight of a second diluent, from about 2% to about 6% by weight of a disintegrant, and from about 0.01% to about 2% by weight of a lubricant, and in particular embodiments, such tablets may include a therapeutically effective amount of R(+) pramipexole, from about 20% to about 50% by weight microcrystalline cellulose, about 10% to about 30% by weight, from about 2% to about 6% crospovidone or croscarmellose, and from about 0.01% to about 2% by weight magnesium stearate. In further embodiments, the pharmaceutical composition may include any amount or combination of microcrystalline cellulose, mannitol, sodium, crospovidone, croscarmellose magnesium stearate, or combination thereof.

In some embodiments, the pharmaceutical compositions including R(+) pramipexole may be prepared as suspensions, solutions or emulsions in oily or aqueous vehicles suitable for injection. In such embodiments, such liquid formulations may further include formulatory agents such as suspending, stabilizing and or dispersing agents formulated for parenteral administration. Such injectable formulations may be administered by any route, for example, subcutaneous, intravenous, intramuscular, intra-arterial or bolus injection or continuous infusion, and in embodiments in which injectable formulations are administered by continuous infusion, such infusion may be carried out for a period of about 15 minutes to about hours. In certain embodiments, formulations for injection can be presented in unit dosage form, e.g., in ampoules or in multi-dose containers, with an added preservative.

In other embodiments, R(+) pramipexole may be formulated as a depot preparation, and such long acting formulations can be administered by implantation (for example subcutaneously or intramuscularly) or by intramuscular injection. Depot injections can be administered at about 1 to about 6 months or longer intervals. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

In still other embodiments, pharmaceutical compositions including R(+) pramipexole may be formulated for buccal or sublingual administration. In such embodiments, the pharmaceutical compositions may be prepared as chewable tablets, flash melts or lozenges formulated in any conventional manner.

In yet other embodiments, pharmaceutical compositions including R(+) pramipexole may be formulated for administration by inhalation. In such embodiments, pharmaceutical compositions may be delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

In further embodiments, pharmaceutical compositions including R(+) pramipexole can be formulated in rectal compositions such as suppositories or retention enemas, e.g., containing conventional suppository bases such as cocoa butter or other glycerides.

In some embodiments, pharmaceutical compositions including R(+) pramipexole may be formulated for transdermal administration. For example, such pharmaceutical compositions may be prepared to be applied to a plaster or applied by transdermal, therapeutic systems that are supplied to the patient. In other embodiments, pharmaceutical and therapeutic compositions including R(+) pramipexole for transdermal administration may include a suitable solid or gel phase carriers or excipients such as, but are not limited to, calcium carbonate, calcium phosphate, various sugars, starches, cellulose derivatives, gelatin, and polymers such as, e.g. polyethyleneglycols. In some embodiments, pharmaceutical compositions including R(+) pramipexole may be administered alone as a single therapeutic agent. In other embodiments, the pharmaceutical compositions including R(+) pramipexole may be administered in combination with one or more other active ingredients, such as, for example, adjuvants, protease inhibitors, or other compatible drugs or compounds where such combination is seen to be desirable or advantageous in achieving the desired effects of the methods described herein.

The embodiments for disease states, patient type (naïve vs. not naïve), daily dose amounts, therapeutically effective amounts, no observable adverse effect level dose amounts, non-effective dose amounts, pharmaceutical compositions, and chiral purities for the methods of the invention, which are described herein separately for the sake of brevity, can be joined in any suitable combination.

Example 1

R(+) Pramipexole Decreases Blood Eosinophils: Results of Two Clinical Trials in Patients with Amyotrophic Lateral Sclerosis Background: In Phase II and Phase III studies of DEX as a potential treatment for ALS, white blood cell status was monitored as a component of routine clinical laboratory assessments and to assess neutropenia.

Methods: The Phase II study randomized 102 subjects and the phase III study randomized 943 subjects in double-blind, placebo controlled trials to assess the safety and efficacy of DEX in ALS, respectively. Subjects were randomized to 25 mg, 75 mg, or 150 mg DEX twice daily or placebo for up to nine months (Phase II) or 150 mg DEX twice daily or placebo for up to 18 months (Phase III). Monthly CBCs were obtained in both studies.

Results: In the two-part, phase II study, a dose-dependent decrease in eosinophil count was observed following 12 weeks of treatment with DEX at doses of 25 mg, 50 mg, and 150 mg twice daily versus placebo (part 1). Following a 4-week, single-blind drug washout, subjects in part 2 who were re-randomized to 150 mg twice daily had a greater decline in eosinophils than subjects re-randomized to 25 mg twice daily. The part 1 decrease in eosinophil count was partially reversed by the end of the 4-week washout period. In Phase III, a profound decrease in blood eosinophil count was observed after 8-12 weeks of treatment with DEX that persisted for the duration of the trial. Counts were reduced by approximately 70% in the treated group, while there was a trend towards increased eosinophil count in patients receiving placebo. The effect was observed in most patients, with 82% of DEX treated subjects experiencing a 50% or greater decline in eosinophil count after 6 months of treatment. ALS is not typically associated with a systemic inflammatory response, and baseline eosinophil counts in the treated and placebo groups were 0.129 and 0.127×109/L, respectively. However, the eosinophil lowering effect of DEX was not diminished in patients (n=42) with higher eosinophil counts (i.e. >0.25×109/L), where a 75% decrease was observed after 6 months of treatment. There were no clinically significant changes in monocytes and lymphocytes. Neutropenia (ANC<1.5×109/L) was observed in 29 DEX treated patients (6.1%) and 8 (1.7%) patients receiving placebo, and was reversible upon withdrawal of treatment. DEX was well-tolerated in Phase II and III trials in ALS subjects.

Conclusions: Clinical experience in over 500 DEX-treated ALS patients demonstrates that DEX produces a slowly-developing, highly-significant persistent eosinophil reduction in humans. As DEX is well-tolerated in humans following exposures up to 18 months, it may represent a novel therapeutic approach for the treatment of eosinophil-associated disorders.

TABLE 1

Safety Data from EMPOWER randomized, double blinded, placebo controlled Phase 3 trial in patients with ALS

| Subjects with: n(%) | Placebo N = 468 | R(+) pramipexole (150 mg twice daily) N = 474 |
|---|---|---|
| Any AE | 447 (96) | 459 (97) |
| Serious adverse event | 233 (50) | 225 (47) |
| Discontinuation due to AE | 36 (8) | 50 (11) |
| Withdrawal due to AE | 59 (13) | 63 (13) |

The EMPOWER trial was designed to be a pivotal study to demonstrate efficacy in slowing the progression of ALS. DEX was well-tolerated relative to placebo and had an acceptable safety profile when administered at 300 mg/day for >12 months in EMPOWER (See Table 1).

Summary of hematology data from clinical trials of patients with ALS: R(+) pramipexole treatment at 300 mg/day decreases several white blood cell counts with the greatest magnitude observed on eosinophils. In ALS patients, statistically significant effects are observed at month 1; effect is maximal by 4 months. Lymphocyte, monocyte, basophil and neutrophil counts are statistically significant, although not clinically relevant. DEX is no less effective when baseline eosinophil counts are elevated. 82% of patients show a decrease of 50% or more in eosinophil count by 6 months of treatment.

Overall Conclusion: Clinical studies in over 500 subjects have shown that 300 mg/day R(+) pramipexole is well tolerated for >12 months. At that dose, R(+) pramipexole produces a slowly-developing, highly-significant persistent eosinophil reduction in humans. The decrease in blood eosinophils is maintained over time and appears to recover after 4 weeks after drug washout. As R(+) pramipexole is well-tolerated in humans following exposures up to 18 months, it may represent a novel therapeutic approach for the treatment of eosinophil-associated disorders Example 2

Effects of Dexpramipexole in an Ovalabumin Pulmonary Inflammation Mouse Model

Female, 6- to 8-wk-old C57BL/6 mice were kept under specific pathogen-free conditions. Mice were immunized intraperitoneally (ip) at days 14 and 21 with chicken egg OVA, adsorbed on 1 mg Al(OH)$_3$ (alum; Sigma-Aldrich) in PBS (OVA/alum model). At day 41 and 42, all mice were exposed to aerosols of OVA/alum of grade III OVA (Sigma-Aldrich) in PBS. In experiments in which dexpramipexole was used, mice received ip injections with 30 mg/kg or 100 mg/kg dexpramipexole before OVA aerosol. Naive mice received challenges with PBS alone. In some experiments, immunized but unchallenged mice were included. Twenty hours after the last OVA challenge, all mice were killed for analysis, bronchoalveolar lavage (BAL) was performed. Results of these experiments are shown in FIG. 7, which demonstrate that dexpramipexole significantly reduced eosinophils in BAL fluid, when compared to untreated group.

Example 3

Dexpramipexole as a Novel Therapy for Eosinophilic Disease

Figure 2:
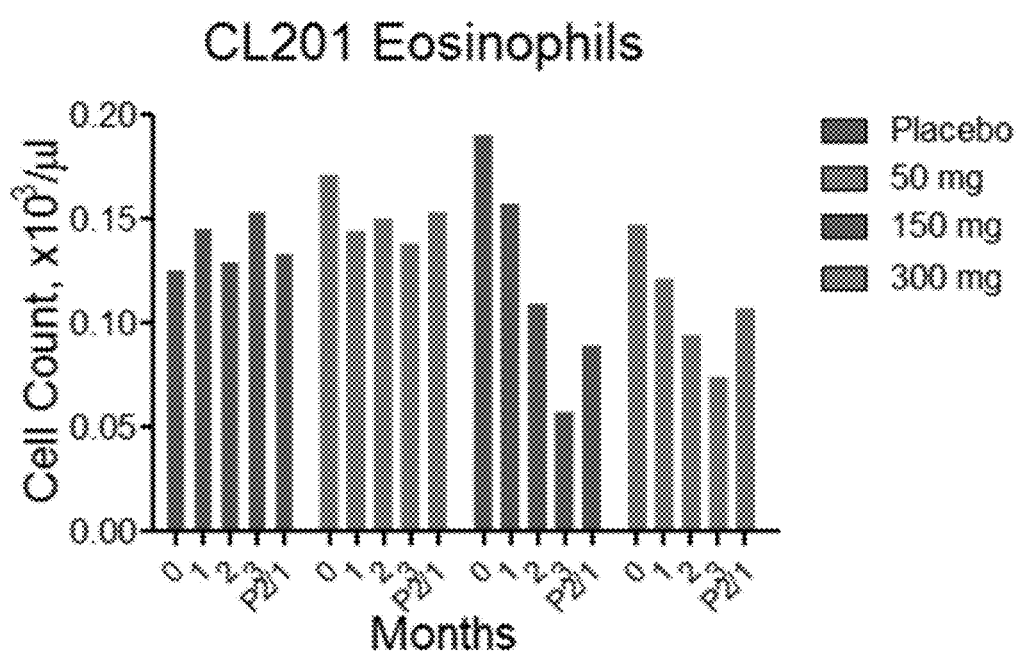
FIG. 2 depicts the dose- and time-dependent effects of R(+) pramipexole on eosinophil counts in CL201. The reduction of eosinophils was observed in human in CL201 (n=22-25 per group). P2/1 is the 4 week washout and new baseline.
Figure 3:
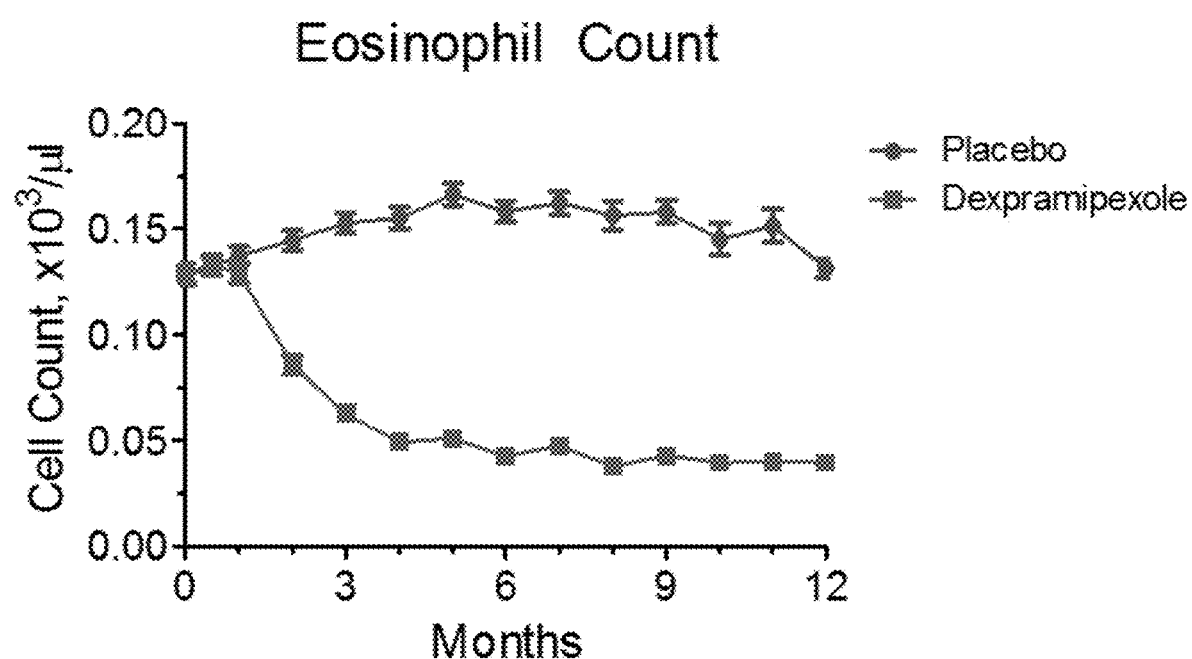
FIG. 3 depicts Hematology data from EMPOWER: Eosinophil count is robustly affected (Mean±SEM, N=474 at baseline, N=328 at 12 months in R(+) pramipexole (DEX) group, 467 and 340 in placebo group).
Figure 4:
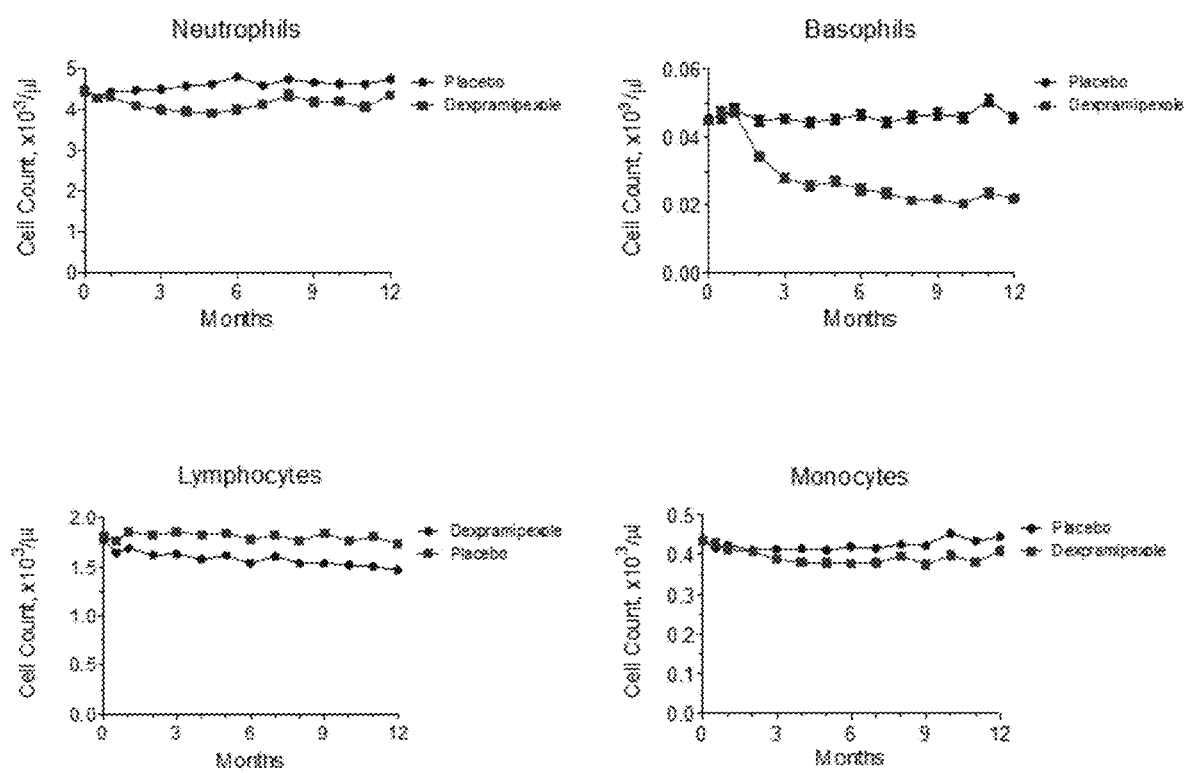
FIG. 4 depicts hematology data from EMPOWER: Effects of R(+) pramipexole on white blood cells (WBCs) (Mean±SEM, N=474 at baseline, N=328 at 12 months in R(+) pramipexole (DEX) group, 467 and 340 in placebo group).
Figure 5:
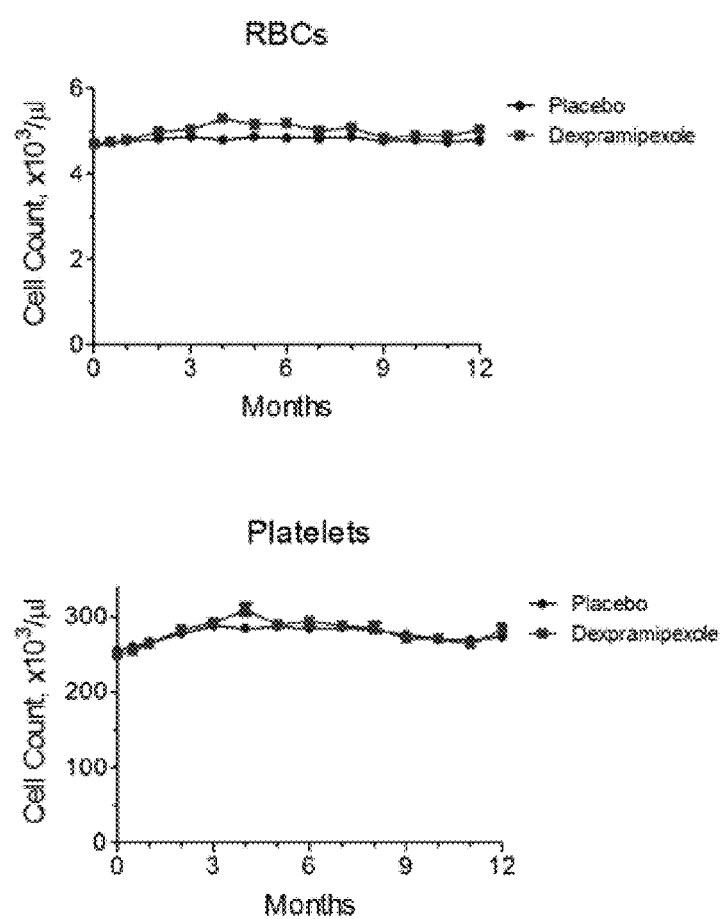
FIG. 5 depicts no effect of R(+) pramipexole on red blood cells (RBCs) and Platelets (Mean±SEM, N=474 at baseline, N=328 at 12 months in R(+) pramipexole (DEX) group, 467 and 340 in placebo group).
Figure 6:
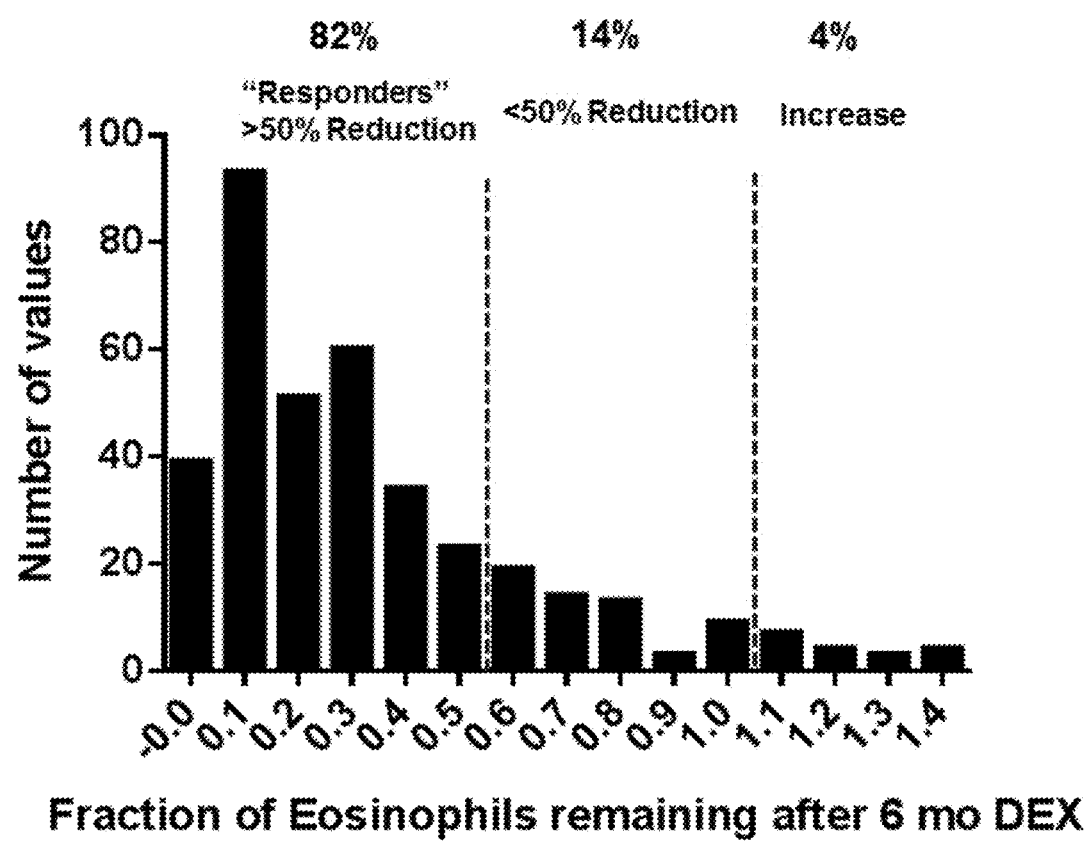
FIG. 6 depicts that 82% of EMPOWER patients showed at least a 50% decrease in eosinophil count.
Figure 8:
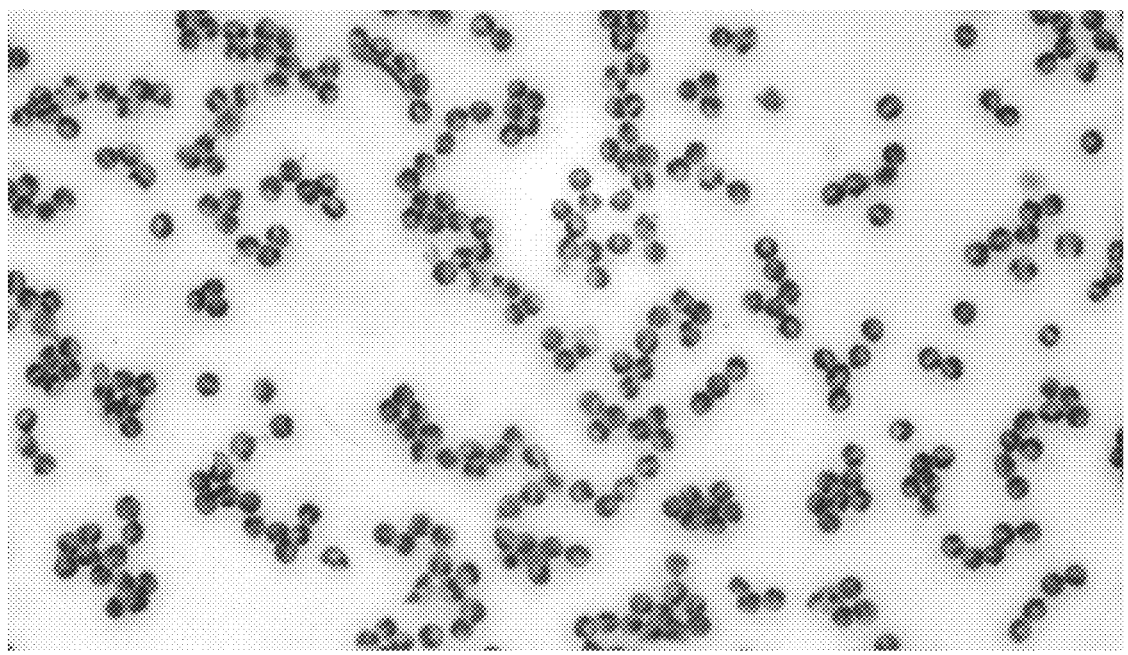
FIG. 8 depicts Giemsa stained isolated human eosinophils.

The effects of dexpramiepexole on eosinophil levels was examined in EMPOWER study. The hematology data collected in EMPOWER revealed a robust effect on blood eosinophil and basophil count in the dexpramipexole treatment group. A re-evaluation of phase 2 clinical data as well as preclinical toxicology data from minipigs also showed an effect of dexpramipexole on eosinophil count. The reduction of eosinophils was observed in the phase 2 study (n=102) and was seen in both parts of the study, with evidence for dose-dependence. This effect was also observed in minipigs in long-term toxicity studies (n=3-5 per group) but not observed in long-term toxicity studies in rats (n=15 per group) (See FIGS. 1-3). FIG. 9 shows that as with the Phase II study, a low incidence of neutropenia in the dexpramipexole treated group was observed which resolved upon dexpramipexole withdrawal.

Analysis of data from all 943 patients is included CBC analysis (performed at baseline, 2 weeks and then monthly for up to 18 months; The numbers of patients with measurements at 16-18 months is very small and these are not included) and a subset of the hematology data is presented. A number of additional parameters were measured but have not been analyzed (E.g. Hematocrit, WBC % values) and no formal statistical comparisons are included here. The subset of patients experiencing neutropenia have not been removed from this analysis.

Figure 10:
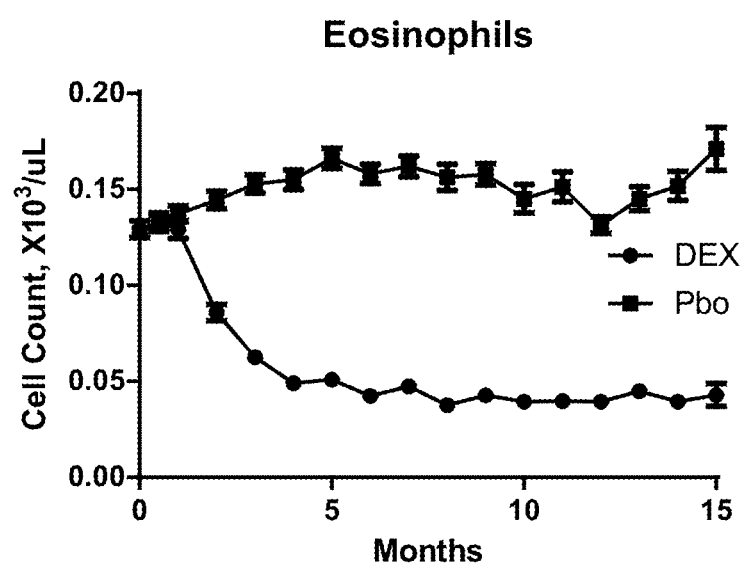
FIG. 10 shows the effect of dexpramipexole on eosinophil counts (Mean±SEM, N=474 at baseline, n=94 at 15 months in Dexpramipexole (DEX) group, 468 and 100 in placebo group).
Figure 11:
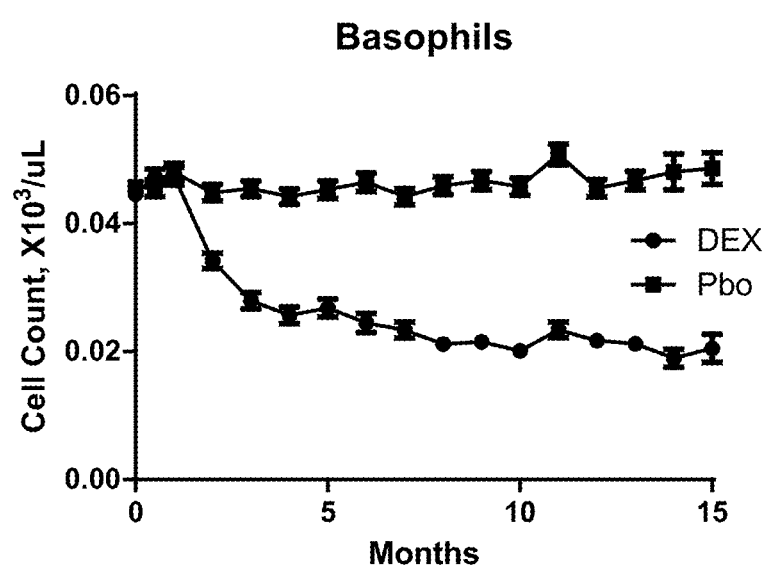
FIG. 11 shows the effect of dexpramipexole on basophil counts (Mean±SEM, N=474 at baseline, n=94 at 15 months in Dexpramipexole (DEX) group, 468 and 100 in placebo group).
Figure 12:
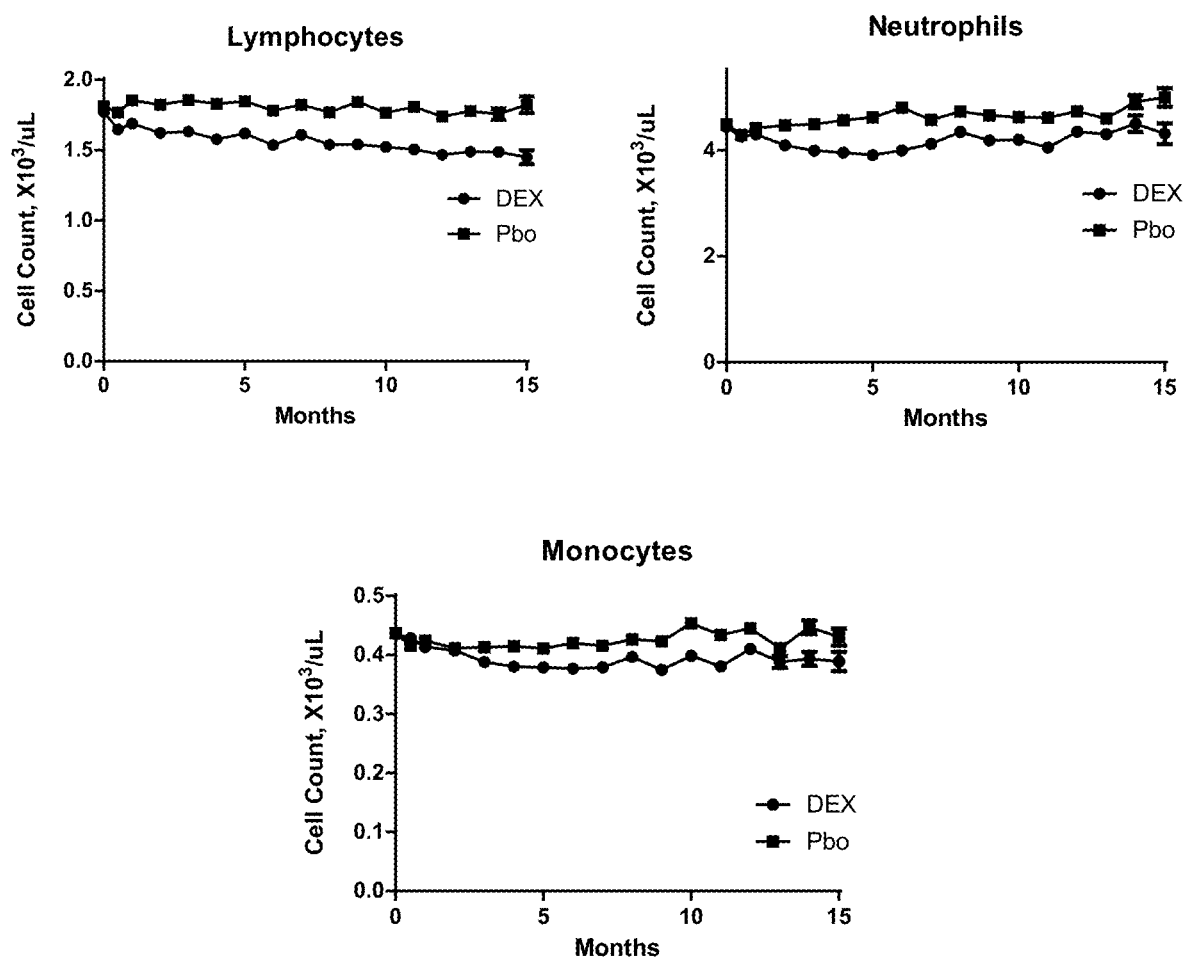
FIG. 12 shows the effect of dexpramipexole on lymphocyte, neutrophil and monocyte counts (Mean±SEM, N=474 at baseline, n=94 at 15 months in Dexpramipexole (DEX) group, 468 and 100 in placebo group).
Figure 13:
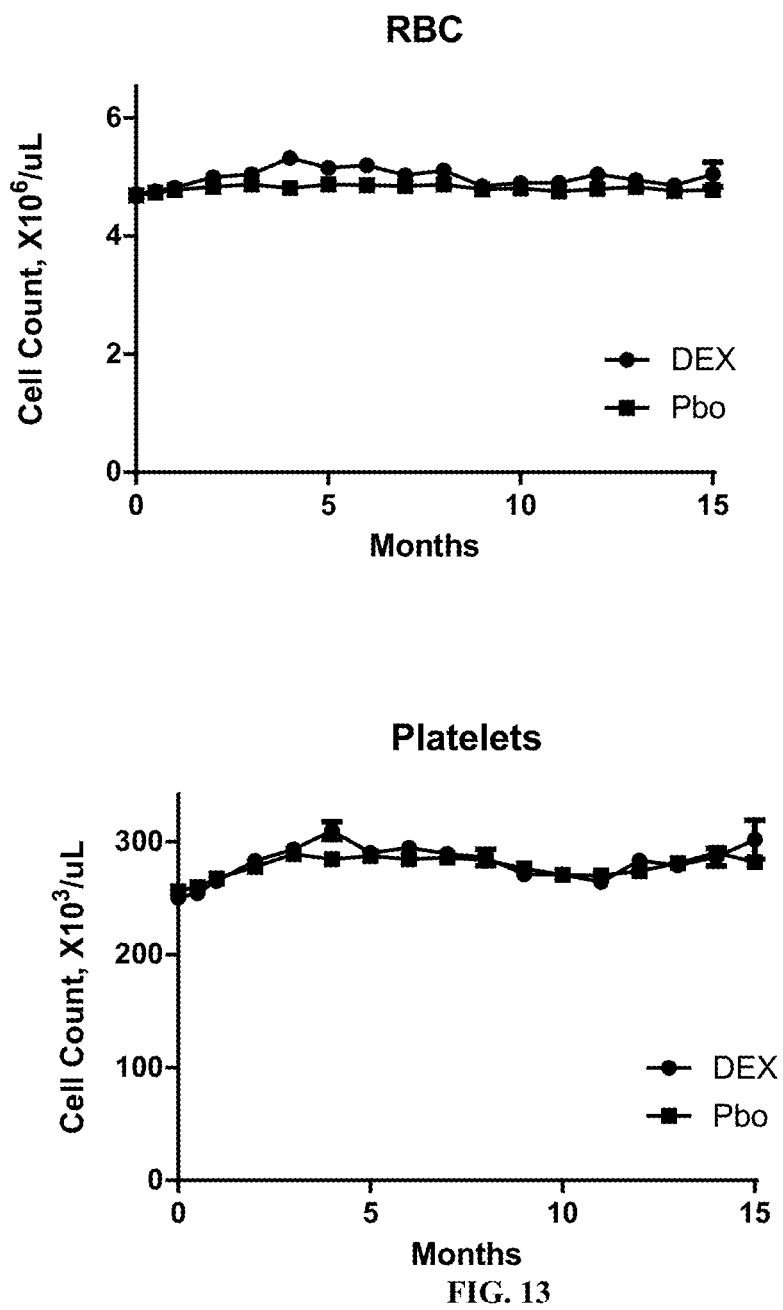
FIG. 13 shows that dexpramipexole had no major impact on other blood cell types (Mean±SEM, N=474 at baseline, n=94 at 15 months in Dexpramipexole (DEX) group, 468 and 100 in placebo group).

FIG. 10 shows the effect of dexpramipexole on eosinophil counts (Mean±SEM, N=474 at baseline, n=94 at 15 months in DEX group, 468 and 100 in placebo group). FIG. 11 shows the effect of dexpramipexole on basophil counts (Mean±SEM, N=474 at baseline, n=94 at 15 months in DEX group, 468 and 100 in placebo group). FIG. 12 shows the effect of dexpramipexole on lymphocyte, neutrophil and monocyte counts (Mean±SEM, N=474 at baseline, n=94 at 15 months in DEX group, 468 and 100 in placebo group). FIG. 13 shows that dexpramipexole had no major impact on other blood cell types (Mean±SEM, N=474 at baseline, n=94 at 15 months in DEX group, 468 and 100 in placebo group).

Figure 14:
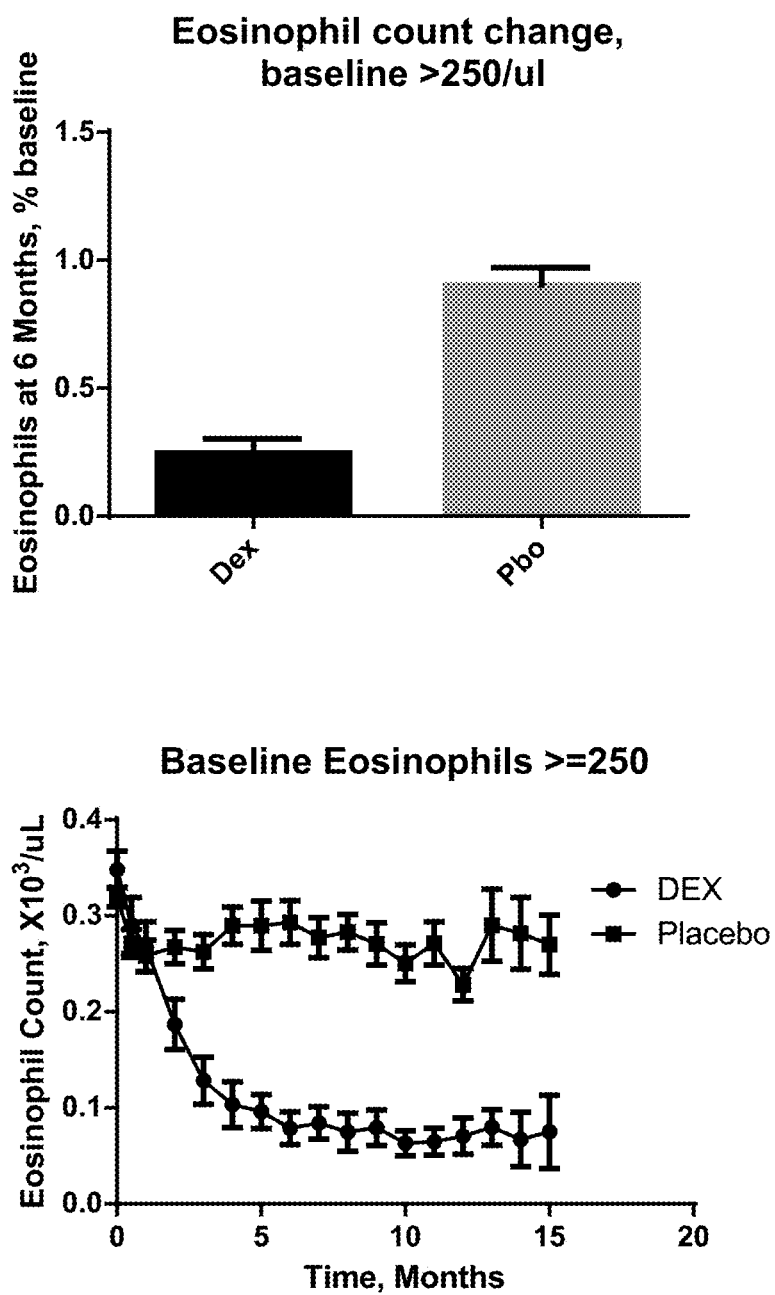
FIG. 14 shows that dexpramipexole decreases eosinophils even when the baseline counts are elevated.
Figure 15:
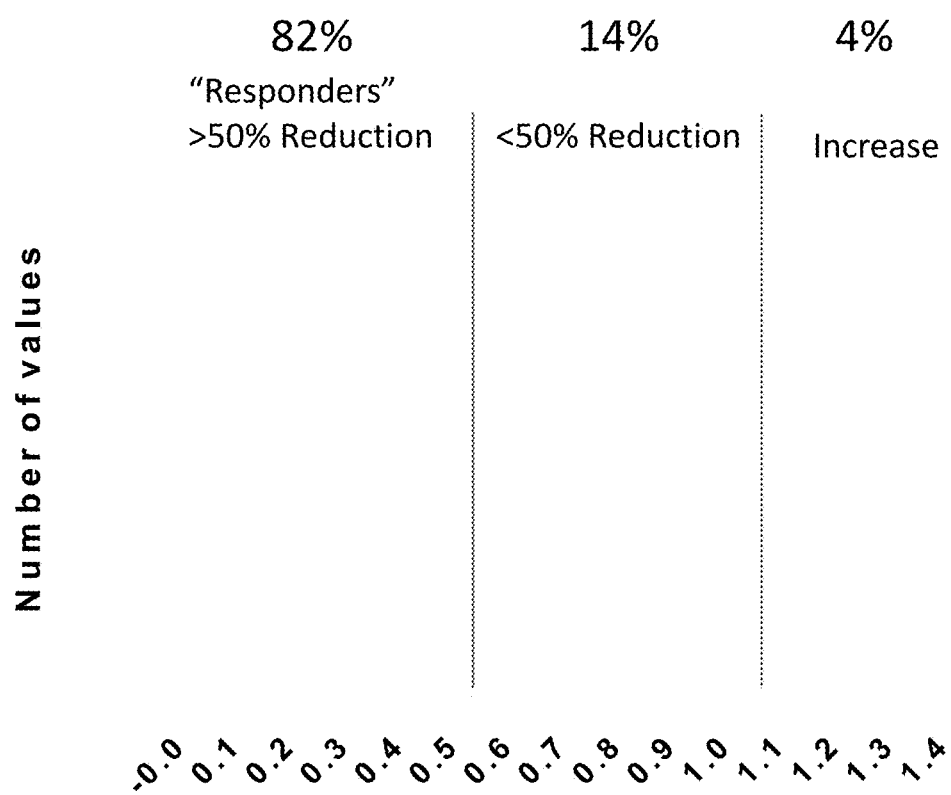
FIG. 15 shows that 82% of patients show a decrease of 50% or more in eosinophil count by 6 months of therapy.

FIG. 14 shows that dexpramipexole decreases eosinophils even when the baseline counts are elevated. Counts of 250 cells per microliter do not represent hypereosinophilia, but represent the top ~10$^{th}$ percentile in this cohort. Dexpramipexole is clearly still effective when the eosinophil count is increased (N=42 DEX patients and 46 placebo patients at baseline, 38 and 40 at 6 months). Additionally, as can be seen in FIG. 15, 82% of patients showed at least a 50% decrease in eosinophil count.

Figure 16:
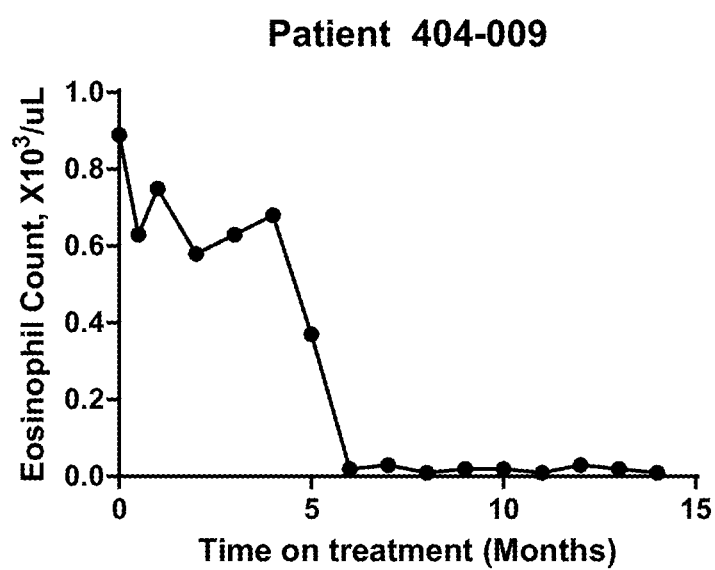
FIG. 16 shows one EMPOWER subject with elevated eosinophil counts at baseline also showed a decrease in eosinophil counts with dexpramipexole treatment.
Figure 17:
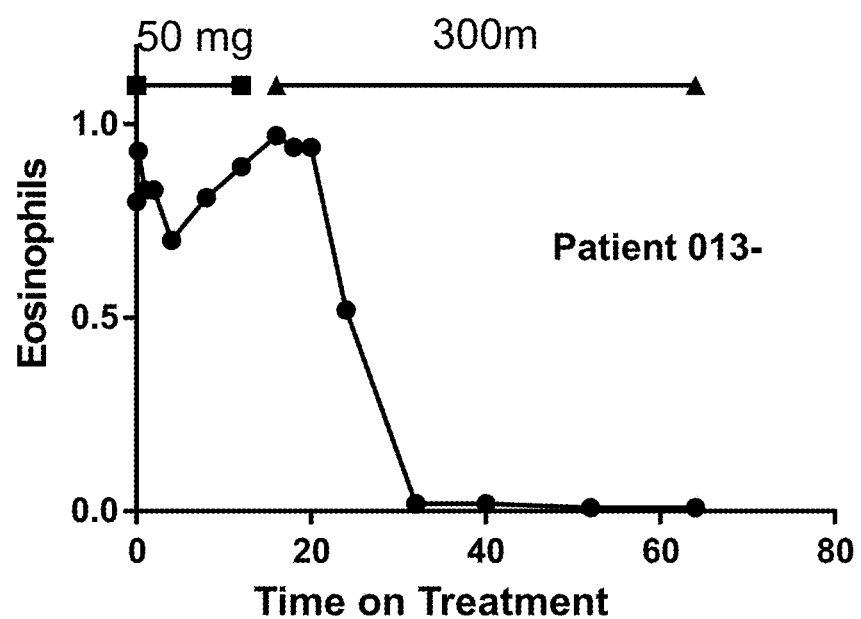
FIG. 17 shows one Phase 2 subject with elevated eosinophil counts at baseline also showed a decrease in eosinophil counts with dexpramipexole treatment.

One EMPOWER subject with elevated eosinophil counts at baseline also showed a decrease in eosinophil counts with dexpramipexole treatment. Subject 404-009 had the highest baseline eosinophil count in the DEX treated group in EMPOWER. The change in eosinophil count in this patient was substantial and prolonged (See FIG. 16). One Phase 2 subject with elevated eosinophil counts at baseline also showed a decrease in eosinophil counts with dexpramipexole treatment. A similar finding was observed in subject 013-050 from the Phase 2 trial (CL201). In Part 1 of the study, the subject was randomized to 50 mg/day. In Part 2, the subject was randomized to 300 mg/day (See FIG. 17).

Figure 18:
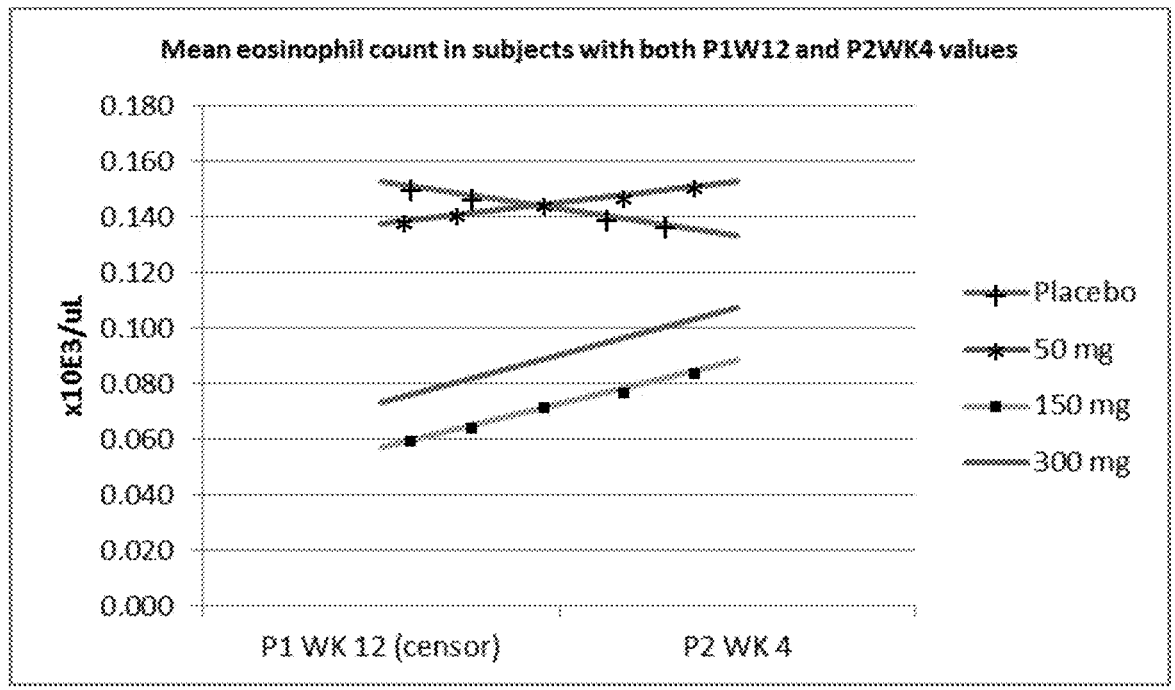
FIG. 18 shows eosinophil counts during a 4-week washout period in Phase 2.
Figure 19:
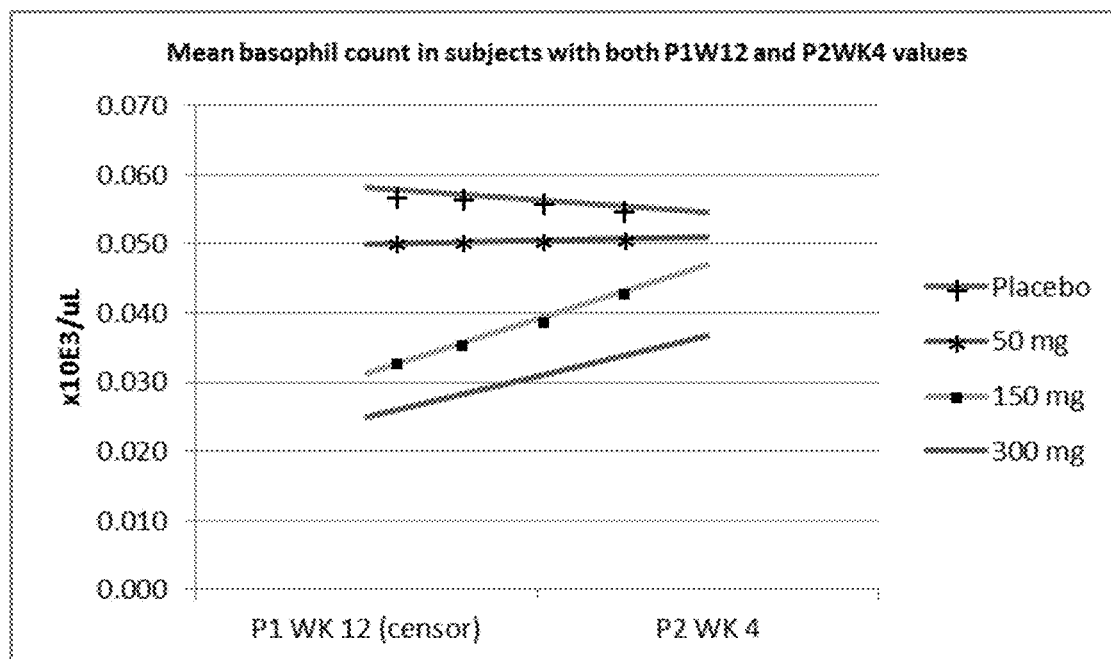
FIG. 19 shows basophil counts during a 4-week washout period in Phase 2.

FIG. 18 shows eosinophil counts during a 4-week washout period in Phase 2. FIG. 19 shows basophil counts during a 4-week washout period in Phase 2.

In summary, dexpramipexole treatment at 300 mg/day decreases eosinophil and basophil counts. No effect is seen at 0.5-1 month and the effect is maximal by 4 months. The decrease in eosinophils is maintained over time and appears to recover after 4 weeks. Lymphocytes, monocytes and neutrophils are not affected in most patients. Dexpramipexole treatment is no less effective when baseline eosinophil counts are elevated. 82% of patients show a decrease of 50% or more in eosinophil count by 6 months of therapy. Clinical studies in over 500 subjects have shown that 300 mg/day dexpramipexole is well tolerated for >12 months. At that dose, dexpramipexole decreases blood eosinophil and basophil count in 2-4 months in most patients.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using "consisting of" or "consisting essentially of" language, rather than "comprising". When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method of treating eosinophilic esophagitis in a human subject comprising: administering to the human subject in need thereof a therapeutically effective amount of R(+) pramipexole or a pharmaceutically acceptable salt thereof.

2. The method of claim 1, wherein the human subject has above about 450 eosinophil cells per microliter in the peripheral blood.

3. The method of claim 1, wherein the therapeutically effective amount is from about 50 mg to about 1,500 mg per day.

4. The method of claim 1, wherein the therapeutically effective amount is from about 150 mg to about 1,500 mg per day.

5. The method of claim 1, wherein the therapeutically effective amount is from about 150 mg to about 300 mg per day.

6. The method of claim 1, wherein administering comprises administering a fraction of the daily dose two or more times per day.

7. The method of claim 1, wherein administering comprises administering a dose equal to about half of a daily dose twice per day.

8. The method of claim 7, wherein the dose is administered every 12 hours.

9. The method of claim 1, wherein administering comprises administering about 150 mg two times per day.

10. The method of claim 1 further comprising monitoring the subject.

11. The method of claim 1 further comprising monitoring the subject for neutropenia.

12. The method of claim 1, further comprising an induction step comprising administering a second therapeutic agent that is capable of decreasing eosinophil levels.

13. The method of claim 12, wherein the second therapeutic agent is selected from a glucocorticoid, a non-steroidal anti-inflammatory drug (NSAIDs), phenolic antioxidants, anti-proliferative drug, or a combination thereof.

14. The method of claim 12, wherein said induction step is from about 1 week to about 6 months.

15. The method of claim 1, wherein said therapeutically effective amount of R(+) pramipexole is about 1,200 mg.

16. The method of claim 1, wherein said therapeutically effective amount of R(+) pramipexole is about 1,500 mg.

17. The method of claim 1, wherein the therapeutically effective amount is about 75 mg two times per day.

18. The method of claim 1, wherein the therapeutically effective amount is about 37.5 mg two times per day.

19. The method of claim 1, wherein the therapeutically effective amount is about 225 mg two times per day.

20. The method of claim 1, wherein the therapeutically effective amount is about 300 mg two times per day.

21. The method of claim 1, wherein said therapeutically effective amount of R(+) pramipexole is about 75 mg per day.

22. The method of claim 1, wherein said therapeutically effective amount of R(+) pramipexole is about 150 mg per day.

23. The method of claim 1, wherein said therapeutically effective amount of R(+) pramipexole is about 300 mg per day.

24. The method of claim 1, wherein said therapeutically effective amount of R(+) pramipexole is about 450 mg per day.

25. The method of claim 1, wherein said therapeutically effective amount of R(+) pramipexole is about 600 mg per day.

26. The method of claim 1, wherein the therapeutically effective amount of R(+) pramipexole, or a pharmaceutically acceptable salt thereof, is administered as an initial dosing regimen followed by administration of a therapeutically effective amount of R(+) pramipexole or a pharmaceutically acceptable salt thereof as a maintenance dosing regimen, wherein the therapeutically effective amount of R(+) pramipexole, or a pharmaceutically acceptable salt thereof, administered during the initial dosing regimen is from about 300 milligrams to about 600 milligrams per day, and wherein the therapeutically effective amount of R(+) pramipexole, or a pharmaceutically acceptable salt thereof, administered during the maintenance dosing regimen is from about 75 milligrams to about 150 milligrams per day.

* * * * *